US009763691B2

(12) United States Patent
Spencer et al.

(10) Patent No.: US 9,763,691 B2
(45) Date of Patent: Sep. 19, 2017

(54) EXPANDABLE SCAFFOLD WITH CUTTING ELEMENTS MOUNTED THERETO

(75) Inventors: Steven Spencer, Minneapolis, MN (US); Richard Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 785 days.

(21) Appl. No.: 13/571,552

(22) Filed: Aug. 10, 2012

(65) Prior Publication Data

US 2013/0041391 A1 Feb. 14, 2013

Related U.S. Application Data

(60) Provisional application No. 61/522,453, filed on Aug. 11, 2011.

(51) Int. Cl.
*A61B 17/3207* (2006.01)
*A61B 17/22* (2006.01)
*A61B 17/221* (2006.01)

(52) U.S. Cl.
CPC .... *A61B 17/320725* (2013.01); *A61B 17/221* (2013.01); *A61B 2017/22038* (2013.01); *A61B 2017/22061* (2013.01)

(58) Field of Classification Search
CPC .......... A61B 17/221; A61B 17/320725; A61B 2017/22038; A61B 2017/22061
USPC ...... 623/1.11, 1.12; 606/159, 191, 194, 200; 604/103.08–103.09
See application file for complete search history.

(56) References Cited

U.S. PATENT DOCUMENTS

| | | | |
|---|---|---|---|
| 3,837,345 A | 9/1974 | Matar | |
| 4,273,128 A | 6/1981 | Lary et al. | |
| 4,765,332 A | 8/1988 | Fischell et al. | |
| 5,009,659 A | 4/1991 | Hamlin et al. | |
| 5,069,679 A | 12/1991 | Taheri | |
| 5,176,693 A * | 1/1993 | Pannek, Jr. | 606/159 |
| 5,196,024 A | 3/1993 | Barath et al. | |
| 5,282,813 A | 2/1994 | Redha et al. | |
| 5,320,634 A | 6/1994 | Vigil et al. | |
| 5,354,279 A | 10/1994 | Hoefling et al. | |

(Continued)

FOREIGN PATENT DOCUMENTS

| | | |
|---|---|---|
| WO | 2007089897 A2 | 8/2007 |
| WO | 2010034021 A2 | 3/2010 |

*Primary Examiner* — Sarah W Aleman
(74) *Attorney, Agent, or Firm* — Seager, Tufte & Wickhem LLP

(57) ABSTRACT

A medical device assembly for incising a stenosis in a blood vessel which includes an incising device, a tubular sheath, and a catheter having an inflatable balloon mounted thereon. The incising device includes a self-expanding scaffold having a plurality of cutting elements projecting radially outward therefrom, and an elongate member extending proximally from the self-expanding scaffold to be manipulated by a user. The self-expanding scaffold is positionable in the lumen of the sheath in a contracted configuration and deployed out of the lumen of the sheath to permit the self-expanding scaffold to expand to an expanded configuration. The inflatable balloon of the catheter is configured to be advanced distally into an interior of the self-expanding scaffold through a proximal opening of the self-expanding scaffold, and inflation of the inflatable balloon urges the cutting elements radially outward to incise a stenosis.

5 Claims, 15 Drawing Sheets

(56) References Cited

U.S. PATENT DOCUMENTS

| | | | |
|---|---|---|---|
| 5,522,825 A | 6/1996 | Kropf et al. | |
| 5,616,149 A | 4/1997 | Barath et al. | |
| 5,649,953 A | 7/1997 | Lefebvre et al. | |
| 5,709,703 A * | 1/1998 | Lukic et al. | 606/198 |
| 5,725,543 A | 3/1998 | Redha et al. | |
| 5,797,935 A | 8/1998 | Barath et al. | |
| 5,902,313 A | 5/1999 | Redha | |
| 6,009,877 A | 1/2000 | Edwards et al. | |
| 6,013,093 A * | 1/2000 | Nott et al. | 606/200 |
| 6,036,708 A * | 3/2000 | Sciver | 606/159 |
| 6,165,187 A | 12/2000 | Reger et al. | |
| 6,423,032 B2 | 7/2002 | Parodi | |
| 6,547,803 B2 | 4/2003 | Seward et al. | |
| 6,551,342 B1 * | 4/2003 | Shen et al. | 606/200 |
| 6,709,444 B1 | 3/2004 | Makower | |
| 6,808,531 B2 | 10/2004 | Lafontaine et al. | |
| 7,127,789 B2 * | 10/2006 | Stinson | 606/108 |
| 7,131,981 B2 * | 11/2006 | Appling et al. | 606/159 |
| 2002/0029052 A1 | 3/2002 | Evans et al. | |
| 2003/0040770 A1 | 2/2003 | Radisch, Jr. | |
| 2005/0021071 A1 | 1/2005 | Konstantino et al. | |
| 2006/0085026 A1 | 4/2006 | Appling et al. | |
| 2006/0173487 A1 * | 8/2006 | Uflacker et al. | 606/198 |
| 2006/0178685 A1 | 8/2006 | Melsheimer | |
| 2007/0213761 A1 * | 9/2007 | Murphy et al. | 606/194 |
| 2010/0241148 A1 | 9/2010 | Schon et al. | |

* cited by examiner

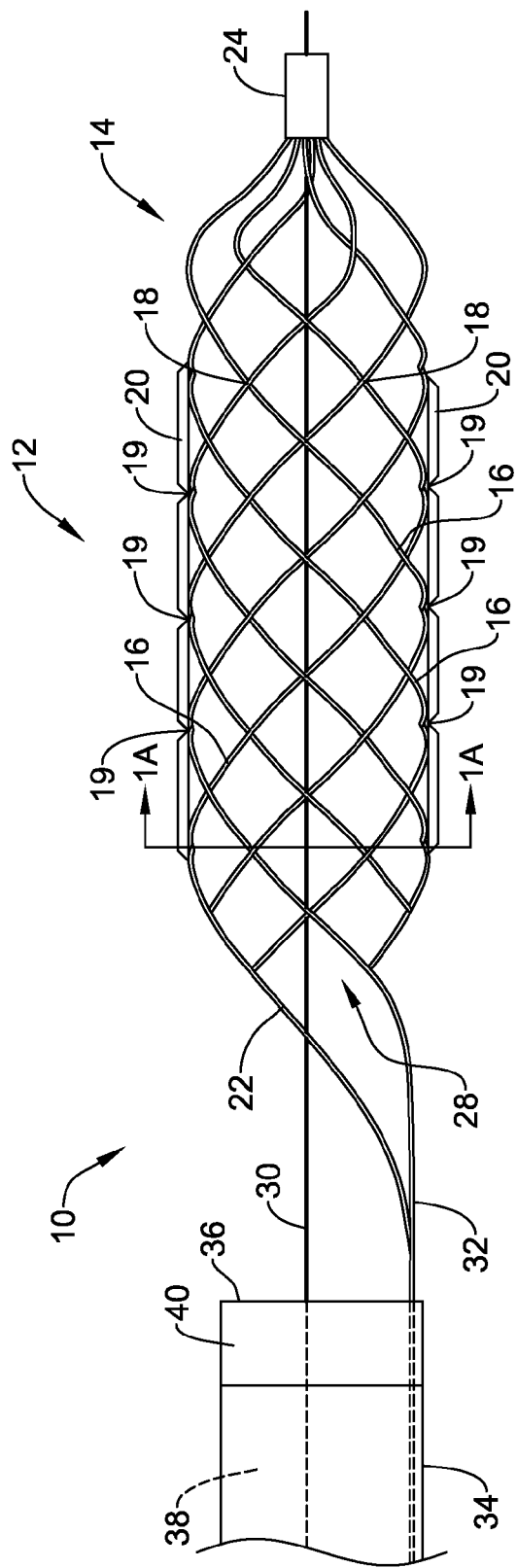
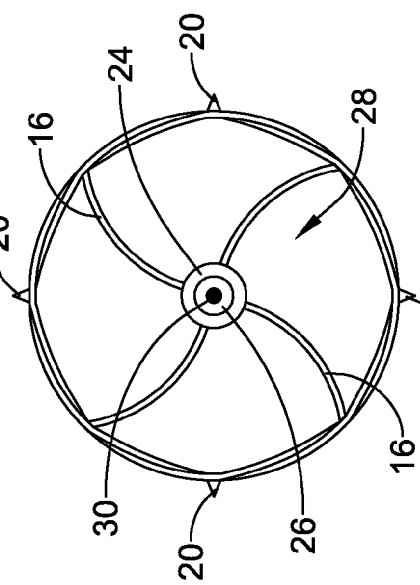
Figure 1
Figure 1A

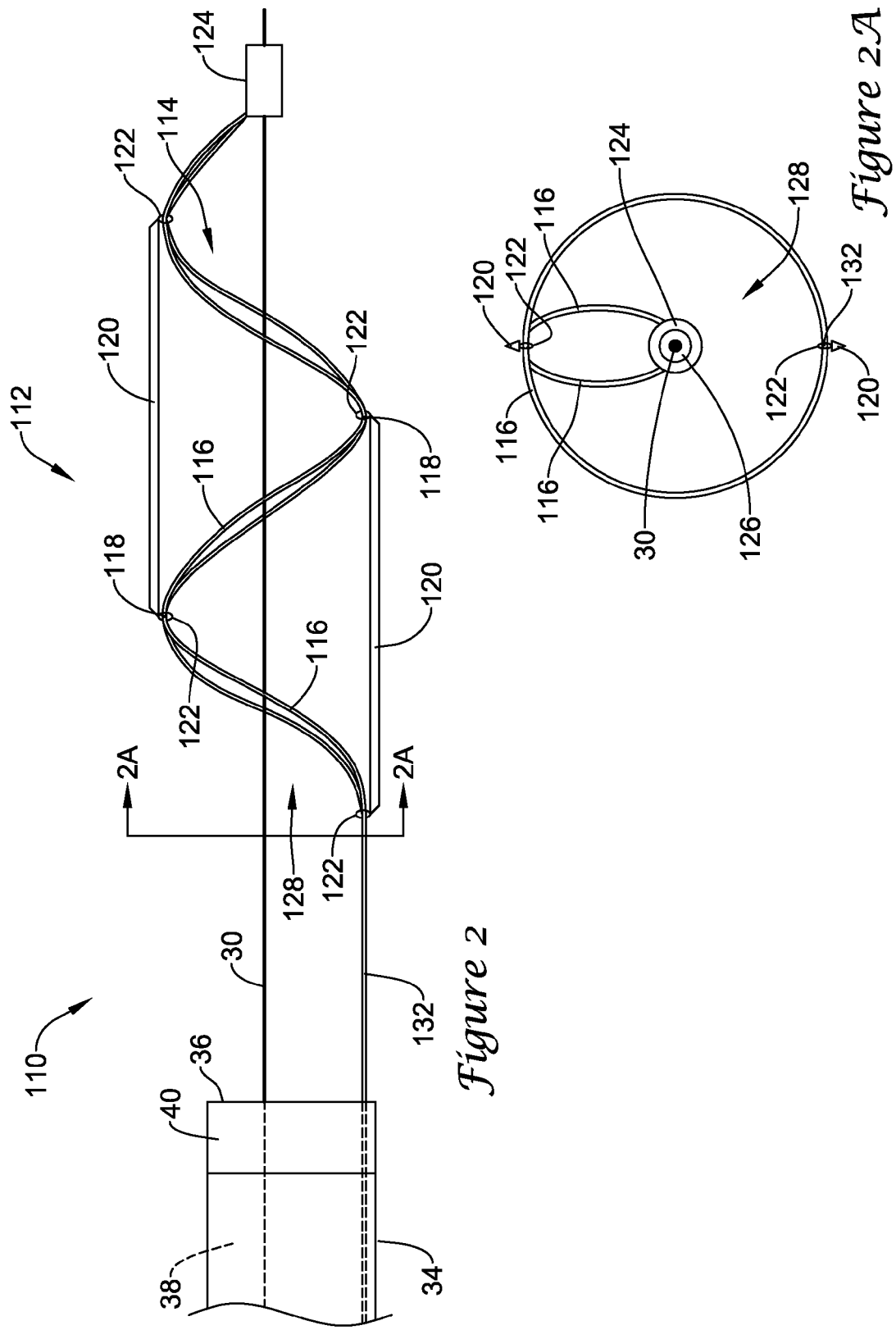

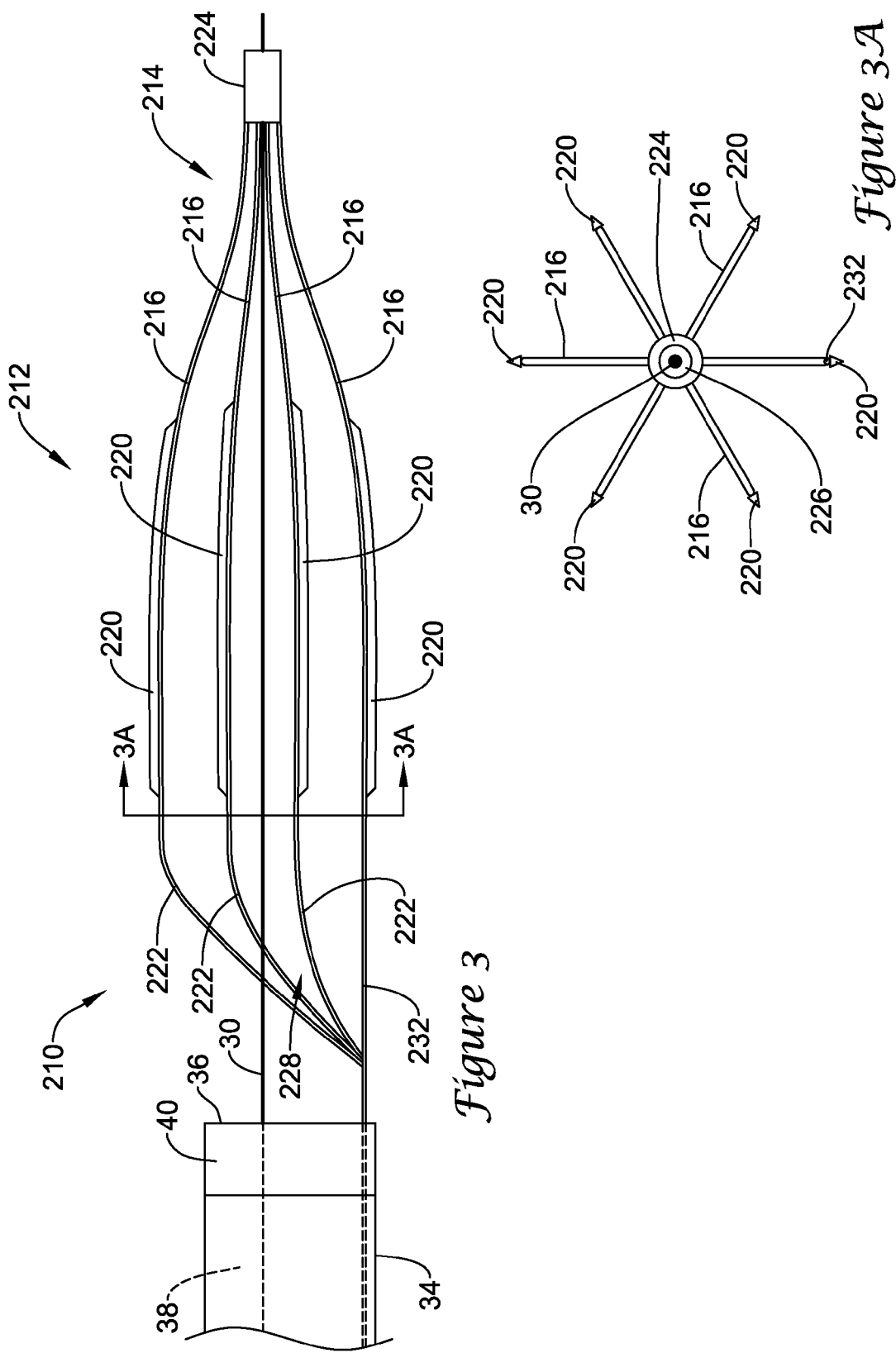

EXPANDABLE SCAFFOLD WITH CUTTING ELEMENTS MOUNTED THERETO

CROSS-REFERENCE TO RELATED APPLICATIONS

This application claims the benefit of U.S. Provisional Application No. 61/522,453, filed on Aug. 11, 2011, the entire disclosure of which is incorporated herein by reference.

TECHNICAL FIELD

The disclosure is directed to expandable scaffolds with cutting elements mounted thereto to score or cut stenotic lesions in a blood vessel. More particularly, the disclosure is directed to self-expanding scaffolds with cutting elements mounted thereto and balloon catheters insertable within the scaffold to radially expand the cutting elements against a stenotic lesion.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action, or lack of oxygenation and/or circulation to other regions of the body.

Occluded, stenotic, or narrowed blood vessels, as well as native or synthetic arteriovenous dialysis fistulae, may be treated in a recanalization procedure, such as with an angioplasty balloon catheter advanced over a guidewire to an occlusion so that the balloon is positioned across the occlusion. The balloon is then inflated to enlarge the passageway through the occlusion.

One of the major obstacles in treating coronary artery disease and/or treating blocked blood vessels or fistulae is re-stenosis or re-narrowing of the passageway through the occlusion subsequent to an angioplasty procedure or other recanalization procedure. Evidence has shown that cutting or scoring the stenosis, for example, with an angioplasty balloon equipped with a cutting element, during treatment can reduce incidence of re-stenosis. Additionally, cutting or scoring the stenosis may reduce trauma at the treatment site and/or may reduce the trauma to adjacent healthy tissue. Cutting elements may also be beneficial additions to angioplasty procedures when the targeted occlusion is hardened, fibrotic or calcified. It is believed typical angioplasty balloons, alone, may not be able to expand certain of these hardened lesions. Thus, angioplasty balloons equipped with cutting elements having cutting edges have been developed to attempt to enhance angioplasty treatments. Existing cutting elements tend to be fairly rigid. The rigid structure of the cutting elements limits the flexibility of the balloon, thereby limiting the ability of the cutting element, and the balloon to which it is mounted, to navigate through a tortuous vasculature of a patient.

Accordingly, there is an ongoing need for delivering cutting elements for use in angioplasty treatments, and methods of incising a stenosis with cutting elements provided with a medical device. Namely, it would be desirable to provide an expandable structure for use with an angioplasty balloon to position cutting elements proximate a stenotic lesion that is flexible for navigating tortuous anatomy.

SUMMARY

The disclosure is directed to several alternative designs, materials and methods of manufacturing medical device structures and assemblies, and the uses thereof.

Accordingly, one illustrative embodiment is a medical device assembly for incising a stenosis in a blood vessel. The medical device assembly includes a self-expanding scaffold configured to be expandable from a first contracted configuration to a second expanded configuration. The self-expanding scaffold is biased toward the second expanded configuration. A cutting element is secured to the self-expanding scaffold and extends radially outward therefrom. The assembly further includes a sheath having a lumen therein. The self-expanding scaffold is positionable in the lumen of the sheath in the first contracted configuration. An elongate member extends proximally from the self-expanding scaffold through the lumen of the sheath. The self-expanding scaffold is constrained in the lumen of the sheath to maintain the self-expanding scaffold in the first contracted configuration and deployed out of the lumen of the sheath to permit the self-expanding scaffold to expand to the second expanded configuration.

Another illustrative embodiment is a medical device assembly for incising a stenosis in a blood vessel. The medical device assembly includes an incising device, a tubular sheath, and a catheter having an inflatable balloon mounted thereon. The incising device includes an expandable scaffold having a plurality of cutting elements projecting radially outward therefrom, and an elongate member extending proximally from the expandable scaffold to be manipulated by a user. The expandable scaffold is positionable in the lumen of the tubular sheath in a contracted configuration with the plurality of cutting elements engaged with an interior of the tubular sheath. The inflatable balloon of the catheter is configured to be advanced distally into an interior of the expandable scaffold through a proximal opening of the expandable scaffold, and inflation of the inflatable balloon urges the cutting elements radially outward to incise a stenosis.

Yet another illustrative embodiment is a method of incising a stenosis in a blood vessel. The method includes advancing a self-expanding scaffold of an incising device in a contracted configuration within a lumen of a tubular sheath to a stenosis in a blood vessel. The self-expanding scaffold includes a plurality of cutting elements projecting radially outward therefrom. The tubular sheath is withdrawn from the self-expanding scaffold to permit the self-expanding scaffold to automatically expand radially outward to an expanded configuration to urge the cutting elements against the stenosis. A deflated balloon of a balloon catheter is advanced into an interior of the self-expanding scaffold through a proximal opening of the self-expanding scaffold with the self-expanding scaffold in the expanded configuration. The balloon is then inflated to press against the interior of the self-expanding scaffold and press the cutting elements into the stenosis.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIG. 1 is a side view of an exemplary system with cutting elements for incising a stenotic lesion;

FIG. 1A is a cross-sectional view of the cutting device of FIG. 1 taken along line 1A-1A;

FIG. 2 is a side view of another exemplary system with cutting elements for incising a stenotic lesion;

FIG. 2A is a cross-sectional view of the cutting device of FIG. 2 taken along line 2A-2A;

FIG. 3 is a side view of another exemplary system with cutting elements for incising a stenotic lesion;

FIG. 3A is a cross-sectional view of the cutting device of FIG. 3 taken along line 3A-3A;

Figure 1B:
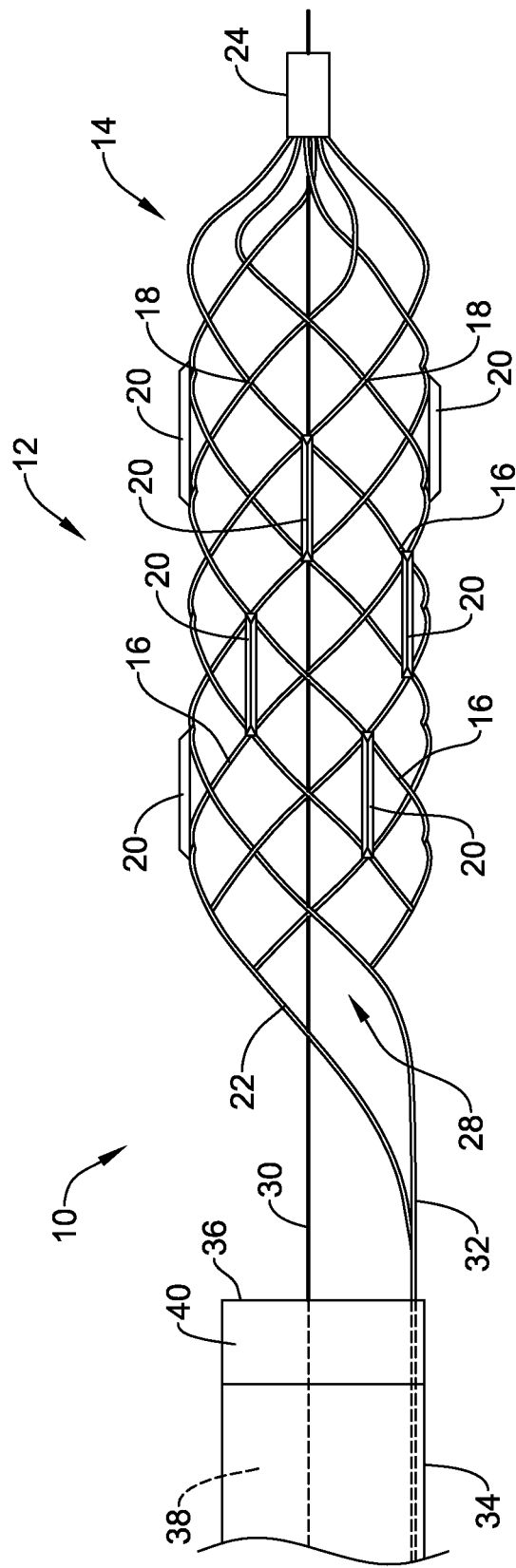
FIG. 1B is a side view of an alternative arrangement of cutting elements mounted on the incising device of FIG. 1.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 is a side view of an exemplary medical device assembly 10 for incising a stenosis in a blood vessel, or other lesion in an anatomical passage. The medical device assembly 10 may include an incising device 12 including one or more, or a plurality of cutting elements 20 for incising or scoring a stenosis within a blood vessel. FIG. 1A is a cross-sectional view taken along line 1A-1A of FIG. 1, further illustrating various features of the incising device 12. The medical device assembly 10 may also include a tubular sheath 34 for delivering the incising device 12 to the stenotic lesion in the blood vessel and/or withdrawing the incising device 12 from the blood vessel in a radially contracted configuration.

The incising device 12 may include an expandable scaffold 14 carrying the one or more, or plurality of cutting elements 20 thereon. In some instances, the expandable scaffold 14 may be a self-expanding scaffold 14 configured to automatically radially expand from a first, contracted configuration when radially constrained to a second, radially expanded configuration when unconstrained. Thus, the self-expanding scaffold 14 may be biased to the radially expanded configuration such that the self-expanding scaffold 14 tends to automatically return to the expanded configuration when all radially constraining forces are removed. In other instances, the expandable scaffold 14 may be expanded from a first, radially contracted configuration to a second radially expanded configuration through the application of an expansion force exerted by an expandable member, an expandable linkage, or other actuatable structure for expanding the scaffold 14.

The expandable scaffold 14 may be formed from any number of biocompatible materials, including polymeric materials, metals, and metal alloys, such as stainless steel, tantalum, or a nickel titanium alloy such as a superelastic nickel titanium alloy known as Nitinol, which may have shape memory properties in some instances.

The expandable scaffold 14 may have any desired construction permitting the expandable scaffold 14 to be radially compressed into the contracted configuration for positioning in the lumen 38 of the sheath 34, yet permitting the expandable scaffold 14 to radially expand to the expanded configuration when unconstrained by the sheath 34. In some instances, the expandable scaffold 14 may be formed of a plurality of interconnected struts, filaments, wires or other expandable framework. For example, as shown in FIG. 1, the expandable scaffold 14 may include a plurality of filaments or wires 16 helically wound into a generally tubular construct. A first subset of the wires 16 may be helically wound in a first direction, while a second subset of the wires 16 may be helically wound in a second, opposite direction. The wires 16 may intersect or cross one another at cross-over points 18. In some instances, the wires 16 may be secured or attached to one another at the cross-over points 18, or the wires 16 may be unsecured and free to move relative to one another at the cross-over points 18.

The proximal end of the expandable scaffold 14 may include a proximal opening 28 opening into the interior of the expandable scaffold 14, allowing access to the interior of the expandable scaffold 14 to permit introducing and positioning a balloon of a balloon catheter therein. In some instances, the expandable scaffold 14 may include an annular hoop at the proximal end to define the proximal opening 28 into the interior of the expandable scaffold 14. The annular hoop may be formed with one or more of the wires 16, or from a discrete member to which the wires 16 may be attached to. In other instances, the proximal opening 28 may be defined by the collective circumferential arrangement of the proximal ends of the wires 16.

The proximal portion of the expandable scaffold 14 may taper radially inward in a proximal direction to facilitate advancing the sheath 34 back over the expandable scaffold 14 to radially contract the expandable scaffold 14 after use of the incising device 12. For instance, the proximal end of the expandable scaffold 14 may have a diameter less than the inner diameter of the sheath 34 such that the sheath 34 may surround the proximal tapered portion as the expandable scaffold 14 is drawn into the lumen 38 of the sheath 34. In some instances, the expandable scaffold 14 may include one or more proximally extending struts 22 to guide the sheath 34 over the expandable scaffold 14 when collapsing the expandable scaffold 14 in the sheath 34 subsequent to using the incising device 12.

The distal end of the helically arranged wires 16 forming the expandable scaffold 14 may converge in a distal direction to a distal tip 24. As shown in FIG. 1A, the wires 16 may extend through an arcuate pathway as the wires taper toward the distal tip 24 from the cylindrical portion of the expandable scaffold 14. In some instances, the distal tip 24 may be constructed of one or more of the wires 16, such as one or more of the wires 16 tightly wound into a coil. In other embodiments, the distal tip 24 may be formed of a discrete tubular member to which the distal ends of the wires 16 may be secured to. The distal tip 24 may be a tubular construction having a lumen 26 extending therethrough for the passage of a guidewire 30. Thus, a guidewire 30 may be disposed in the lumen 26 of the distal tip 24, such that the expandable scaffold 14 of the incising device 12 may be advanced over the guidewire 30 to a treatment site. In some instances, the distal tip 24, and thus the guidewire 30 extending through the central lumen 26 of the distal tip 24, may be arranged coaxially with the expandable scaffold 14, such that a balloon of a balloon catheter advanced over the guidewire 30 into the interior of the expandable scaffold 14 is coaxially positioned within the expandable scaffold 14.

The cutting elements 20 may vary in number, position, and arrangement about the expandable scaffold 14. For example, the incising device 12 may include one, two, three, four, five, six, or more cutting elements 20 that are disposed at any position along the expandable scaffold 14 and in a regular, irregular, or any other suitable pattern. For example, in some embodiments the incising device 12 may include a plurality of cutting elements 20 longitudinally arranged symmetrically around the circumference of the expandable scaffold 14.

In some instances, the cutting elements 20 may include multiple cutting segments with flexible regions 19 between adjacent segments to increase the flexibility of the cutting elements 20. In some instances, adjacent segments of the cutting elements 20 may be interconnected with a flexible link, while in other instances adjacent segments of the cutting elements 20 may be spaced from one another at the flexible regions 19.

In some instances, such as shown in FIG. 1B, the incising device 12 may include a plurality of cutting elements 20 off-set from one another around the circumference of the expandable scaffold 14. For example, the incising device 12 may include one or more, or a plurality of cutting elements 20 radially offset from, as well as longitudinally offset from one or more, or a plurality of adjacent cutting elements 20. Thus, the cutting elements 20 may be staggered both radially and longitudinally around the circumference of the expandable scaffold 14.

The cutting elements 20 may be made from any suitable material such as a metal, metal alloy, polymer, metal-polymer composite, and the like, or any other suitable material. For example, cutting elements 20 may be made from stainless steel, titanium, nickel-titanium alloys, tantalum, iron-cobalt-nickel alloys, or other metallic materials in some instances.

As shown in FIG. 1, the cutting elements 20 may be mounted to and project radially outward from the expandable scaffold 14. In other embodiments, the wires 16 of the expandable scaffold 14 may define the cutting elements 20 for scoring or cutting tissue. The cutting elements 20 may be secured to the wires 16 of the expandable scaffold 14 such as by welding, brazing, soldering, crimping, adhesively bonding, thermal bonding, or other desired means. In some instances, the cutting elements 20 may be secured to the expandable scaffold 14 at one or more of the cross-over points 18 of the wires 16. In some embodiments, it may be desirable to secure the opposing ends of the cutting elements 20 to wires 16 of the expandable scaffold 14, such as at cross-over points 18 of the wires 16.

The cutting elements 20 may be secured to the generally cylindrical portion of the expandable scaffold 14, such that the cutting elements 20 may extend in a generally longitudinal direction parallel to the central longitudinal axis of the expandable scaffold 14. In other instances, the cutting elements 20 may be helically arranged around the circumference of the expandable scaffold 14, or arranged in another desired configuration. The cutting elements 20 may extend any desired extent of the expandable scaffold 14. For example, the cutting elements 20 may be secured intermediate the proximal and distal extents of the generally cylindrical portion of the expandable scaffold 14.

As described later herein, a balloon 52, or other radially expandable member of a catheter 50 may be positioned in the interior of the expandable scaffold 14 to provide a radially outward force to urge the cutting elements 20 radially outward and press the cutting elements 20 against a stenosis or other tissue. In some instances, a balloon of a catheter may be integrally incorporated with the incising device 12, and thus pre-inserted within the expandable scaffold 14 of the incising device 12 prior to using the incising device 12 in a medical procedure. In other instances, however, the incising device 12 may be provided without a balloon 52 pre-inserted within the expandable scaffold 14, thus allowing a physician to select any desired balloon 52 or other radially expandable member of a catheter 50 to be inserted within the expandable scaffold 14 intra-operatively, and/or allow for exchanging between a plurality of different sizes of balloons 52 intra-operatively.

The incising device 12 may also include an elongate member 32 extending proximally from the expandable scaffold 14 to be manipulated by a physician during a medical procedure. The elongate member 32 may have sufficient rigidity to be pushed distally (e.g., apply an axially compressive force) and pulled proximally (e.g., apply an axially tensile force) to manipulate the expandable scaffold 14. The elongate member 32, which may be a tubular member or a solid member in some instances, may have a length sufficient to extend from the treatment site to a handle assembly (not shown) of the medical device assembly 10 located external of the patient such that medical personnel can actuate the elongate member 32 to manipulate the expandable scaffold 14. For example, the elongate member 32 may extend through the lumen 38 of the tubular sheath 34 adjacent to and generally parallel to the guidewire 30 to a handle assembly of the sheath 34. The elongate member 32 may be non-coaxially connected to the expandable scaffold 14, such as attached to the expandable scaffold 14 at a peripheral location offset from the central longitudinal axis of the expandable scaffold 14, and thus offset from the guidewire 30. In some instances, one or more struts 22 may extend from the expandable scaffold 14 to the elongate member 32.

The sheath 34 may be a tubular member having a lumen 38 extending therethrough opening out at a distal opening 36 of the tubular sheath 34. The lumen 38 of the sheath 34 may have an inner diameter sized to receive the expandable scaffold 14 therein in the radially contracted configuration. The expandable scaffold 14 may be positioned in the lumen 38 of the tubular sheath 34 in the contracted configuration with the cutting elements 20 engaged with an interior surface of the tubular sheath 34. The elongate member 32 may extend proximally through the lumen 38 to the proximal end of the sheath 34. Likewise, the guidewire 30 may extend through the lumen 38 of the sheath 34 along an exterior surface of the elongate member 32.

While the sheath 34 may be formed of a flexible polymeric tubing for navigating a vasculature, the sheath 34 may include a protective distal tip 40 configured to withstand scoring from the cutting elements 20 as the incising device 12 is advanced out of the lumen 38 through the distal opening 36 and/or withdrawn into the lumen 38 through the distal opening 36. For instance, the protective distal tip 40 may include a metal annular band, a tubular braid member, a helical coil, or other reinforcing structure providing the protective distal tip 40 sufficient rigidity to withstand cutting forces exerted on the protective distal tip 40 from contact with the cutting elements 20. In other instances, the protective distal tip 40 may include an impact resistant polymer having a hardness or durability sufficient to withstand cutting forces exerted on the protective distal tip 40 from contact with the cutting elements 20.

FIG. 2 is a side view of another exemplary medical device assembly 110 for incising a stenosis in a blood vessel, or other lesion in an anatomical passage. The medical device assembly 110 may include an incising device 112 including one or more, or a plurality of cutting elements 120 for incising or scoring a stenosis within a blood vessel. FIG. 2A is a cross-sectional view taken along line 2A-2A of FIG. 2, further illustrating various features of the incising device 112. Similar to the medical device assembly 10 of FIG. 1, the medical device assembly 110 may also include a tubular sheath 34 for delivering the incising device 112 to the stenotic lesion in the blood vessel and/or withdrawing the incising device 112 from the blood vessel.

The incising device 112 may be similar to the incising devise 12 in many respects. For example, the incising device 112 may include an expandable scaffold 114 carrying the one or more, or plurality of cutting elements 120 thereon, and be configured to radially expand from a first, contracted configuration when radially constrained to a second, radially expanded configuration when unconstrained. In some instances, the expandable scaffold 114 may be a self-expanding scaffold 114 configured to automatically radially expand from the first, contracted configuration when radially constrained to the second, radially expanded configuration when unconstrained. Thus, the self-expanding scaffold 114 may be biased to the radially expanded configuration such that the self-expanding scaffold 114 tends to automatically return to the expanded configuration when all radially constraining forces are removed. In other instances, the expandable scaffold 114 may be expanded from the first, radially contracted configuration to the second radially expanded configuration through the application of an expansion force exerted by an expandable member, an expandable linkage, or other actuatable structure for expanding the scaffold 114.

The expandable scaffold 114 may have any desired construction permitting the expandable scaffold 114 to be radially compressed into the contracted configuration for positioning in the lumen 38 of the sheath 34, yet permitting the expandable scaffold 114 to radially expand to the expanded configuration when unconstrained by the sheath 34. For example, as shown in FIG. 2, the expandable scaffold 114 may include a plurality of filaments or wires 116 helically wound with a first wire 116 helically wound in a first direction and a second wire 116 helically wound in a second, opposite direction. The wires 116 may intersect or cross one another at cross-over points 118. In some instances, the wires 116 may be secured or attached to one another at the cross-over points 118, or the wires 116 may be unsecured and free to move relative to one another at the cross-over points 118. The incising device 112 may also include an elongate member 132 extending proximally from the expandable scaffold 114 through the lumen 38 of the sheath 34 to be manipulated by a physician during a medical procedure. In some instances, the elongate member 132 may be formed as a proximal extension of one or more of the wires 116 or as a discrete member secured to the proximal ends of the wires 116, for example.

The expandable scaffold 114 may include a proximal opening 128 opening into the interior of the expandable scaffold 114, allowing access to the interior of the expandable scaffold 114 to permit introducing and positioning a balloon of a balloon catheter therein. In some instances, the proximal opening 128 may be defined by the proximal most arcuate winding of the wires 116 from the elongate member 132 to the first proximal most cross-over point 118 of the wires 116.

The distal end of the helically arranged wires 116 forming the expandable scaffold 114 may terminate at a distal tip 124. As shown in FIG. 2A, the wires 116 may extend through an arcuate pathway of a smaller radius of curvature as the wires taper toward the distal tip 124 from the cylindrical portion of the expandable scaffold 114. Similar to the distal tip 24, the distal tip 124 may be constructed of one or more of the wires 116, or the distal tip 124 may be formed of a discrete tubular member to which the distal ends of the wires 116 may be secured to, having a lumen 126 extending therethrough for the passage of a guidewire 30. In some instances, the distal tip 124, and thus the guidewire 30 extending through the central lumen 126 of the distal tip 124, may be arranged coaxially with the expandable scaffold 114, such that a balloon of a balloon catheter advanced over the guidewire 30 into the interior of the expandable scaffold 114 is coaxially positioned within the expandable scaffold 114.

The cutting elements 120 may vary in number, position, and arrangement about the expandable scaffold 114. For example, the incising device 112 may include one, two, three, four, five, six, or more cutting elements 120 that are disposed at any position along the expandable scaffold 114 and in a regular, irregular, or any other suitable pattern. For example, in some embodiments the incising device 112 may include a plurality of cutting elements 120 longitudinally arranged symmetrically around the circumference of the expandable scaffold 114.

As shown in FIG. 2, the cutting elements 120 may be mounted to and project radially outward from the expandable scaffold 114. In other embodiments, the wires 116 of the expandable scaffold 114 may define the cutting elements 120 for scoring or cutting tissue.

As shown in FIG. 2, in some instances, the cutting elements 120 may be mounted to the expandable scaffold 114 such that the wires 116 may be translatable relative to the cutting elements 120. For example, the cutting elements 120 may include grommets or collars 122 through which the wires 116 slidably extend through, allowing the cutting elements 120 to float on the wires 116. In such instances, the expandable scaffold 114 may be collapsed by longitudinally extending the wires 116 such that the connection between the cutting elements 120 and the wires 116 at the collars 122 translates along the wires 116 as the wires 116 are elongated. In some instances, the cutting elements 120 may be configured such that a cutting edge of the cutting element 120 is oriented radially outward to contact a vessel wall or stenosis regardless of the rotational orientation of the cutting element 120 about its longitudinal axis.

In other instances, the cutting elements 120 may be secured to the wires 116 of the expandable scaffold 114 such as by welding, brazing, soldering, crimping, adhesively bonding, thermal bonding, or other desired means. In some instances, the cutting elements 120 may be secured to the cylindrical portion of the expandable scaffold 114 at one or more of the cross-over points 118 of the wires 116. In some embodiments, it may be desirable to secure the opposing ends of the cutting elements 120 to wires 116 of the expandable scaffold 114, such as at cross-over points 118 of the wires 116. For example, a first cutting element 120 may have a proximal end secured to the wires 116 at the proximal terminus of the expandable scaffold 114 and a distal end secured to the wires 116 at a cross-over point 118 distal of the proximal terminus of the expandable scaffold 114. A second cutting element 120, which may be secured to the expandable scaffold 114 on an opposite side of the expandable scaffold as the first cutting element 120, may have a proximal end secured to a proximal cross-over point 118 and a distal end secured to a distal cross-over point 118. The first cutting element 120 may be offset longitudinally from the first cutting element 120 as the securement locations (e.g., cross-over points 118) on opposite sides of the expandable scaffold 114 may be alternately arranged axially along the expandable scaffold 114.

As described later herein, a balloon 52, or other radially expandable member of a catheter 50 may be positioned in the interior of the expandable scaffold 114 to provide a radially outward force to urge the cutting elements 120 radially outward and press the cutting elements 120 against a stenosis or other tissue. In some instances, a balloon of a catheter may be integrally incorporated with the incising device 112, and thus pre-inserted within the expandable scaffold 114 of the incising device 112 prior to using the incising device 112 in a medical procedure. In other instances, however, the incising device 112 may be provided without a balloon 52 pre-inserted within the expandable scaffold 114, thus allowing a physician to select any desired balloon 52 or other radially expandable member of a catheter 50 to be inserted within the expandable scaffold 114 intra-operatively, and/or allow for exchanging between a plurality of different sizes of balloons 52 intra-operatively.

FIG. 3 is a side view of another exemplary medical device assembly 210 for incising a stenosis in a blood vessel, or other lesion in an anatomical passage. The medical device assembly 210 may include an incising device 212 including one or more, or a plurality of cutting elements 220 for incising or scoring a stenosis within a blood vessel. FIG. 3A is a cross-sectional view taken along line 3A-3A of FIG. 3, further illustrating various features of the incising device 212. Similar to the medical device assembly 10 of FIG. 1, the medical device assembly 210 may also include a tubular sheath 34 for delivering the incising device 212 to the stenotic lesion in the blood vessel and/or withdrawing the incising device 212 from the blood vessel.

The incising device 212 may be similar to the incising devise 12 in many respects. For example, the incising device 212 may include an expandable scaffold 214 carrying the one or more, or plurality of cutting elements 220 thereon, and be configured to radially expand from a first, contracted configuration when radially constrained to a second, radially expanded configuration when unconstrained. In some instances, the expandable scaffold 214 may be a self-expanding scaffold 214 configured to automatically radially expand from the first, contracted configuration when radially constrained to the second, radially expanded configuration when unconstrained. Thus, the self-expanding scaffold 214 may be biased to the radially expanded configuration such that the self-expanding scaffold 214 tends to automatically return to the expanded configuration when all radially constraining forces are removed. In other instances, the expandable scaffold 214 may be expanded from the first, radially contracted configuration to the second radially expanded configuration through the application of an expansion force exerted by an expandable member, an expandable linkage, or other actuatable structure for expanding the scaffold 214.

The expandable scaffold 214 may have any desired construction permitting the expandable scaffold 214 to be radially compressed into the contracted configuration for positioning in the lumen 38 of the sheath 34, yet permitting the expandable scaffold 214 to radially expand to the expanded configuration when unconstrained by the sheath 34. For example, as shown in FIG. 3, the expandable scaffold 214 may include a plurality of struts 216 extending longitudinally along the expandable scaffold 214. The struts 216, which may be wires or other filaments in some instances, may be circumferentially arranged uniformly or nonuniformly around the circumference of the expandable scaffold 214. The incising device 212 may also include an elongate member 232 extending proximally from the expandable scaffold 214 through the lumen 38 of the sheath 34 to be manipulated by a physician during a medical procedure. In some instances, the elongate member 232 may be formed as a proximal extension of one or more of the struts 216 or as a discrete member secured to the expandable scaffold 214, for example. A one or more, or a plurality of additional extension wires 222 may extend from the expandable scaffold 214 to the elongate member 232, providing a tapered transition from the elongate member 232 to struts 216 of the expandable scaffold 214 to facilitate drawing the expandable scaffold 214 into the sheath 34. In some instances, the proximally extending extension wires 222 may be unitarily formed from the struts 216, or the extension wires 222 may be discrete members extending between the elongate member 232 and the struts 216. The circumferentially arranged extension wires 222 may define a proximal opening 228 opening into the interior of the expandable scaffold 214, allowing access to the interior of the expandable scaffold 214 to permit introducing and positioning a balloon of a balloon catheter therein. The proximal tapered portion provided by the extension wires 222 may facilitate positioning the sheath 34 back over the expandable scaffold 214 to radially contract the expandable scaffold 214 after use of the incising device 212. For instance, the one or more proximally extending extension wires 222 may help guide the sheath 34 over the expandable scaffold 214 when collapsing the expandable scaffold 214 in the sheath 34 subsequent to using the incising device 212.

The longitudinal struts 216 may extend axially to define a cylindrical portion of the expandable scaffold 214, and then taper radially inward near the distal end of the expandable scaffold 214 to converge at a distal tip 224. The distal tip 224 may be a tubular member having a lumen 226 extending therethrough for the passage of a guidewire 30. In some instances such as shown in FIG. 3A, the distal tip 224, and thus the guidewire 30 extending through the central lumen 226 of the distal tip 224, may be arranged coaxially with the expandable scaffold 214, such that a balloon of a balloon catheter advanced over the guidewire 30 into the interior of the expandable scaffold 214 is coaxially positioned within the expandable scaffold 214.

The cutting elements 220 may vary in number, position, and arrangement about the expandable scaffold 214. For example, the incising device 212 may include one, two, three, four, five, six, or more cutting elements 220 that are disposed at any position along the expandable scaffold 214 and in a regular, irregular, or any other suitable pattern. For example, in some embodiments the incising device 212 may include a plurality of cutting elements 220 longitudinally arranged symmetrically around the circumference of the expandable scaffold 214.

As shown in FIG. 3, the cutting elements 220 may be mounted to and project radially outward from the struts 216 of the expandable scaffold 214. In other embodiments, the struts 216 of the expandable scaffold 214 may define the cutting elements 220 for scoring or cutting tissue. The cutting elements 220 may be secured to the struts 216 of the expandable scaffold 214 such as by welding, brazing, soldering, crimping, adhesively bonding, thermal bonding, or other desired means.

As described later herein, a balloon 52, or other radially expandable member of a catheter 50 may be positioned in the interior of the expandable scaffold 214 to provide a radially outward force to urge the cutting elements 220 radially outward and press the cutting elements 220 against a stenosis or other tissue. In some instances, a balloon of a catheter may be integrally incorporated with the incising device 212, and thus pre-inserted within the expandable scaffold 214 of the incising device 212 prior to using the incising device 212 in a medical procedure. In other instances, however, the incising device 212 may be provided without a balloon 52 pre-inserted within the expandable scaffold 214, thus allowing a physician to select any desired balloon 52 or other radially expandable member of a catheter 50 to be inserted within the expandable scaffold 214 intra-operatively, and/or allow for exchanging between a plurality of different sizes of balloons 52 intra-operatively.

FIGS. 4-8 illustrate an exemplary method of treating a stenotic lesion with an expandable scaffold with cutting elements in cooperation with an inflatable balloon of a balloon catheter. Although the exemplary method will be described in regards to using the incising device 12, it is understood that such a method of treating a stenosis may be performed using the incising device 112 described in FIG. 2, the incising device 212 described in FIG. 3, or a similarly configured incising device in accordance with this disclosure.

The medical device assembly 10 may be navigated through the lumen 92 of a blood vessel 90 to a treatment location proximate a stenosis 94 or other tissue to be treated which may be within any suitable peripheral or cardiac vessel lumen location. For instance, the incising device 12 may be loaded in the sheath 34 with the expandable scaffold 14 constrained in the contracted position within the lumen 38 of the sheath 34 prior to advancing the medical device assembly 10 through the blood vessel 90. Alternatively, the sheath 34 may be initially placed proximate the stenosis 94, and subsequently the incising device 12 may be inserted into the lumen 38 and pushed distally through the sheath 34 to the treatment site.

Figure 4:
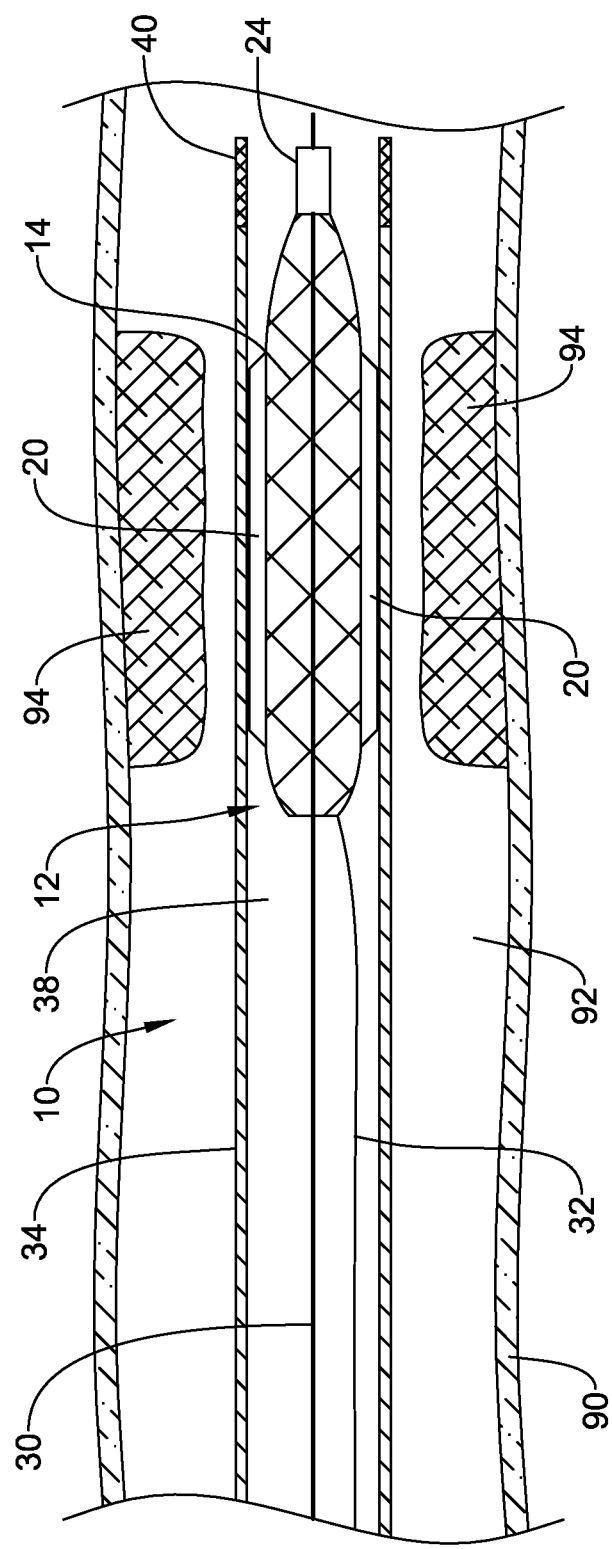
FIGS. 4-8 illustrate an exemplary method of treating a stenotic lesion with an expandable scaffold with cutting elements in cooperation with an inflatable balloon of a balloon catheter.

The distal tip 24 of the incising device 12 may be inserted over a guidewire 30, with the guidewire 30 extending through the interior of the expandable scaffold 14 and through the lumen 38 of the sheath 34. As shown in FIG. 4, the expandable scaffold 14 of the incising device 12 may be advanced in the contracted configuration over the guidewire 30 while constrained within the lumen 38 of the tubular sheath 34 to the stenosis 94 in the blood vessel 90. The guidewire 30 may extend along and adjacent to the elongate member 32 of the incising device 12 within the lumen 38 of the sheath 34.

Figure 5:
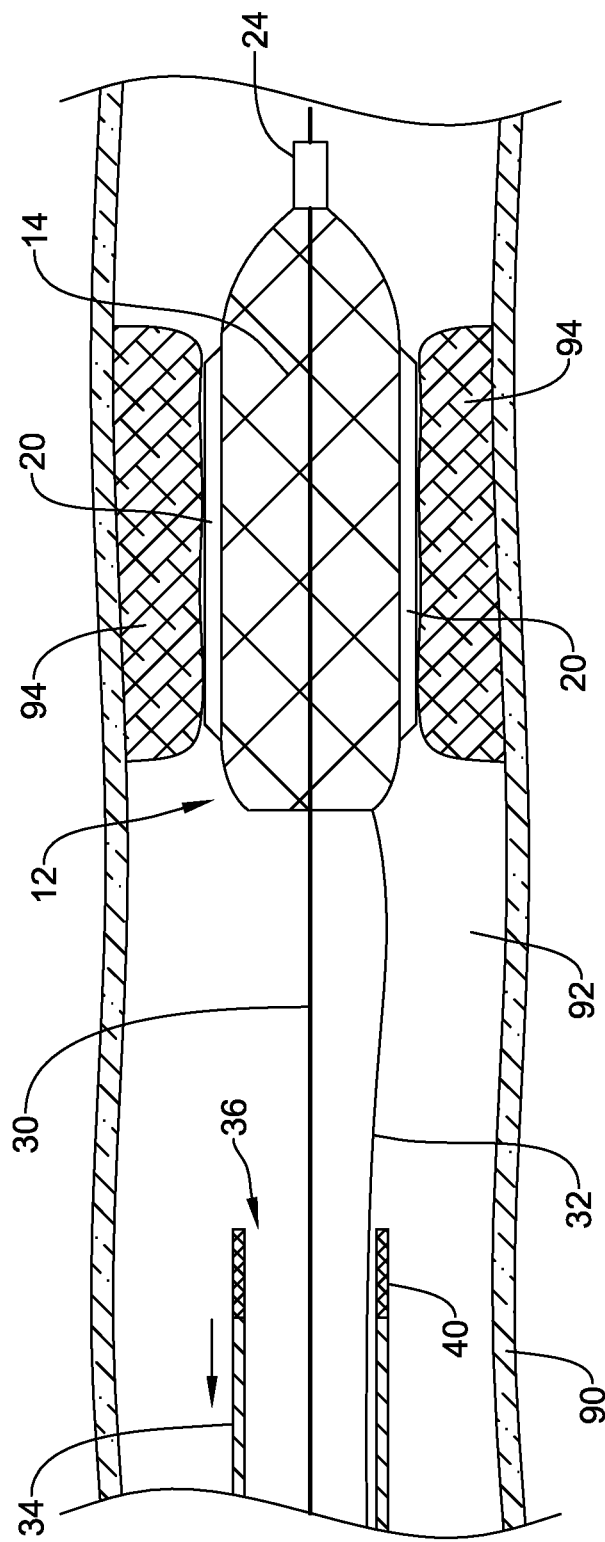

As shown in FIG. 5, with the radially constrained expandable scaffold 14 positioned across the stenosis 94 within the sheath 34, the sheath 34 may be withdrawn proximally to deploy the expandable scaffold 14 distally from the distal opening 36 of the tubular sheath 34. For example, the physician may hold the elongate member 32 of the incising device 12 while pulling the sheath 34 proximally to maintain the expandable scaffold 14 in a desired position as the sheath 34 is withdrawn. Alternatively, the physician may push the elongate member 32 distally while holding the sheath 34 to expel the expandable scaffold 14 from the distal opening 36 of the sheath 34. The protective distal tip 40 of the sheath 34 may withstand scoring from the cutting elements 20 as the incising device 12 is advanced out of the lumen 38 through the distal opening 36. Once unconstrained by the sheath 34, the expandable scaffold 14 may automatically radially expand toward the expanded configuration. The expandable scaffold 14 may be sized such that in the expanded configuration, the cutting elements 20 may contact and/or press against the stenosis 94.

Figure 6:
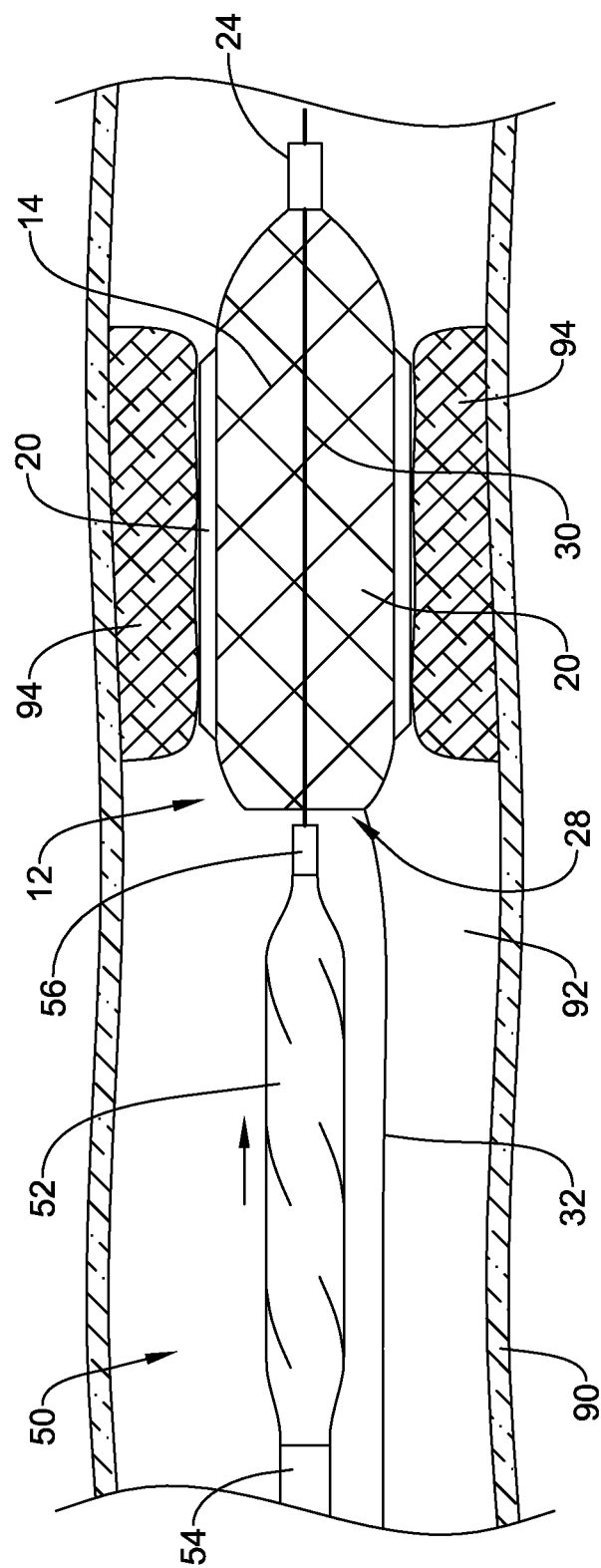

As shown in FIG. 6, a deflated balloon 52, or other expandable member, of a catheter 50 (if not already disposed in the interior of the expandable scaffold 14 prior to deploying the incising device 12 across the stenosis 94) may be advanced distally over the guidewire 30 through the proximal opening 28 into the interior of the expandable scaffold 14 with the expandable scaffold 14 in the expanded configuration. The catheter 50 may be selected by the physician based on the desired inflated diameter of the balloon 52 for a particular medical procedure. For example, the balloon 52 chosen may be selected based on the diameter of the vessel to be treated, the size of the stenosis, and/or the amount of radial expansion of the expandable scaffold 14 desired. In some instances, the catheter 50 may be advanced over the guidewire 30 through the lumen 38 of the sheath 34, or the sheath 34 may be completely withdrawn from the patient prior to advancing the catheter 50 over the guidewire 30.

In some instances, the balloon 52 may be formed of a compliant material, a semi-compliant material, or a non-compliant material. The balloon 52 may be made from typical angioplasty balloon materials including polymers such as polyethylene terephthalate (PET), polytetrafluoroethylene (PTFE), ethylene tetrafluoroethylene (ETFE), polybutylene terephthalate (PBT), polyurethane, polyvinylchloride (PVC), polyether-ester, polyester, polyamide, elastomeric polyamides, polyether block amide (PEBA), as well as other suitable materials, or mixtures, combinations, copolymers thereof, polymer/metal composites, and the like. The balloon 52 may be configured so that the balloon 52 includes one or more "wings" or wing-shaped regions when the balloon 52 is deflated.

The catheter 50 may include a catheter shaft 54 secured to the balloon 52 and extending proximally therefrom. The catheter shaft 54 may be similar to typical catheter shafts. For example, the catheter shaft 54 may include an outer tubular member and an inner tubular member extending through at least a portion of the outer tubular member. The tubular members may be arranged in any appropriate way. For example, in some embodiments the inner tubular member can be disposed coaxially within the outer tubular member. Alternatively, the inner tubular member may follow the inner wall or otherwise be disposed adjacent the inner wall of the outer tubular member. In other embodiments, the tubular members may be arranged in another desired fashion.

The inner tubular member may include an inner lumen, such as a guidewire lumen for receiving the guidewire 30 therethrough. Accordingly, the catheter 50 can be advanced over the guidewire 30 to the desired location. The guidewire lumen may extend along essentially the entire length of the catheter shaft 54 such that catheter 50 resembles traditional "over-the-wire" catheters. Alternatively, the guidewire lumen may extend along only a portion of the catheter shaft 54 such that the catheter 50 resembles "single-operator-exchange" or "rapid-exchange" catheters.

The catheter shaft 54 may also include an inflation lumen that may be used, for example, to transport inflation media to and from the balloon 52 to selectively inflate and/or deflate the balloon 52. The location and position of the inflation lumen may vary, depending on the configuration of the tubular members of the catheter shaft 54. For example, when the outer tubular member surrounds the inner tubular member, the inflation lumen may be defined within the space between the tubular members. In embodiments in which the outer tubular member is disposed alongside the inner tubular member, then the inflation lumen may be the lumen of the outer tubular member.

The balloon 52 may be coupled to the catheter shaft 54 in any of a number of suitable ways. For example, the balloon 52 may be adhesively or thermally bonded to the catheter shaft 54. In some embodiments, a proximal waist of the balloon 52 may be bonded to the catheter shaft 54, for example, bonded to the distal end of the outer tubular member, and a distal waist of the balloon 52 may be bonded to the catheter shaft 54, for example, bonded to the distal end of the inner tubular member. The exact bonding positions, however, may vary.

In some instances, the catheter 50 may be properly positioned within the interior of the expandable scaffold 14 when the distal tip 56 of the catheter 50 contacts a proximal end of the distal tip 24 of the incising device 12. As the balloon 52 and catheter 50 may be advanced over the guidewire 30, which extends centrally through the expandable scaffold 14, the balloon 52 may likewise be concentrically positioned within the interior of the expandable scaffold 14.

Figure 7:
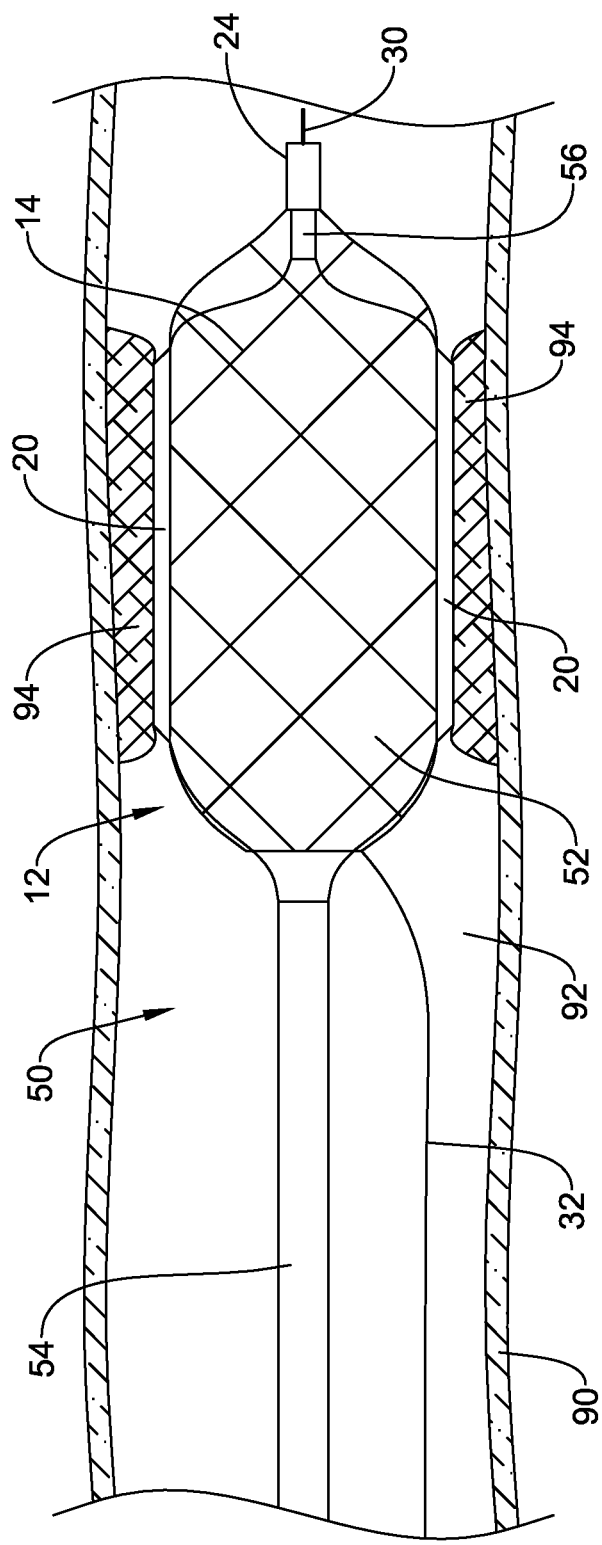

As shown in FIG. 7, once positioned within the interior of the expandable scaffold 14, the balloon 52 can be inflated to exert a radially outward force on the interior of the expandable scaffold 14 to further enlarge the expandable scaffold 14 and/or to urge the cutting elements 20 further radially outward to penetrate into or score the stenosis 94. Thus, the cutting elements 20 may cut or score the stenosis 94 to facilitate enlarging the lumen proximate the stenosis 94.

Subsequently, the balloon 52 may be deflated and withdrawn proximally from the interior of the expandable scaffold 14 through the proximal opening 28 of the expandable scaffold 14 with the expandable scaffold 14 in the expanded configuration. In some instances, it may be desirable to advance a second balloon of a second balloon catheter over the guidewire 30 into the interior of the expandable scaffold 14 through the proximal opening 28 of the expandable scaffold 14 with the expandable scaffold 14 in the expanded configuration. For example, the first balloon 52 of the first catheter 50 may have a first inflated diameter and the second balloon 52 of the second catheter 50 may have a second inflated diameter greater than the inflated diameter of the first balloon 52. Thus, the first balloon 52 may be used to radially expand the expandable scaffold to a first diameter and urge the cutting elements 20 into the stenosis 94 a first amount, and then the first balloon 52 and catheter 50 may be exchanged for the second balloon 52 and catheter 50 to further expand the expandable scaffold to a second diameter greater than the first diameter and urge the cutting elements further into the stenosis 94 a second amount, greater than the first amount. The balloons 52 may be sequentially exchanged for balloons 52 of a different size (e.g., of a sequentially greater size), as desired until a desired dilatation of the blood vessel 90 has been attained.

Figure 8:
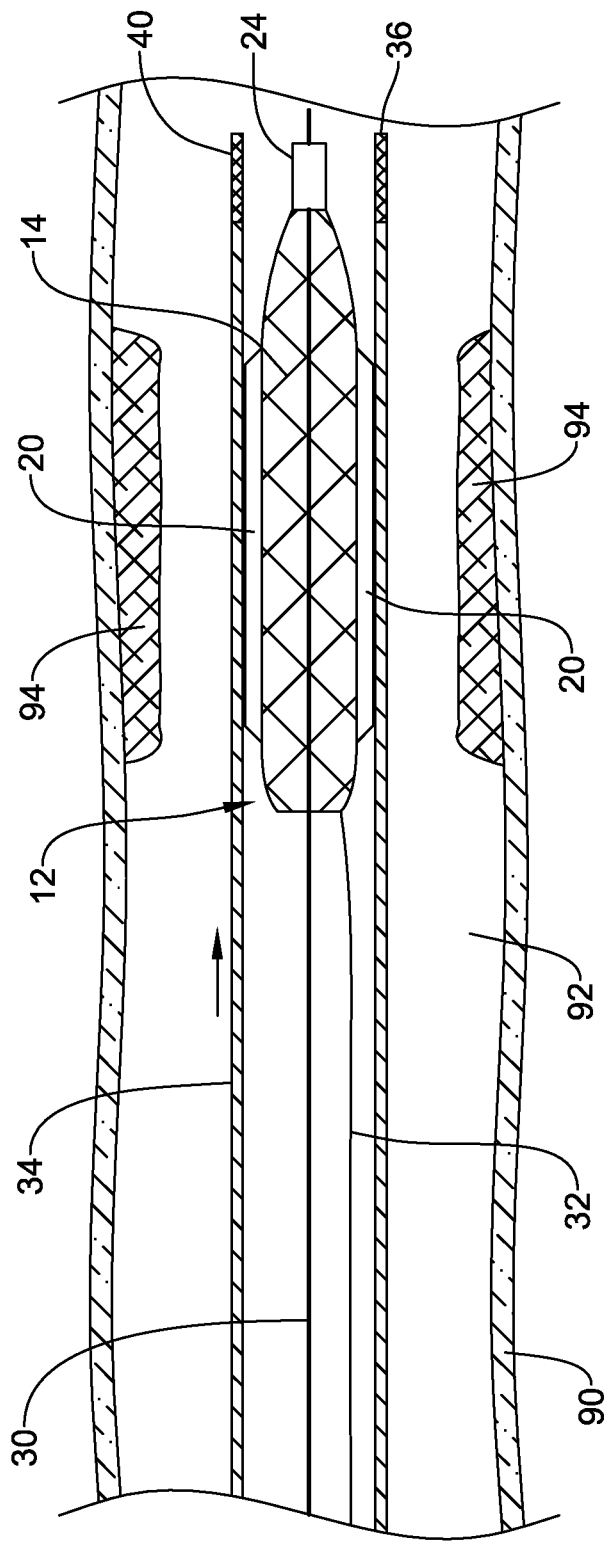

As shown in FIG. 8, once the desired treatment of the blood vessel 90 with the incising device 12 has been achieved, the incising device 12 may be recaptured and retrieved with the sheath 34, and then withdrawn from the blood vessel 90. For example, as shown in FIG. 8, the sheath 34, or another sheath, may be advanced distally to the expandable scaffold 14. The physician may grasp the elongate member 32 to hold the expandable scaffold 14 stationary while advancing the sheath 34 distally over the expandable scaffold 14 to collapse the expandable scaffold 14 into the lumen 38 of the sheath 34, or the physician may pull the elongate member 32 proximally to pull the self-expanding scaffold 14 into the distal opening 36 of the sheath 34 to collapse the expandable scaffold 14 into the lumen 38 of the sheath 34. The protective distal tip 40 of the sheath 34 may withstand scoring from the cutting elements 20 as the incising device 12 is refracted into the lumen 38 through the distal opening 36. The sheath 34 and incising device 12 may then be withdrawn from the blood vessel 90, leaving the guidewire 30 in place for navigating additional medical devices across the stenosis 94 in the blood vessel 90, if desired.

Figure 9:
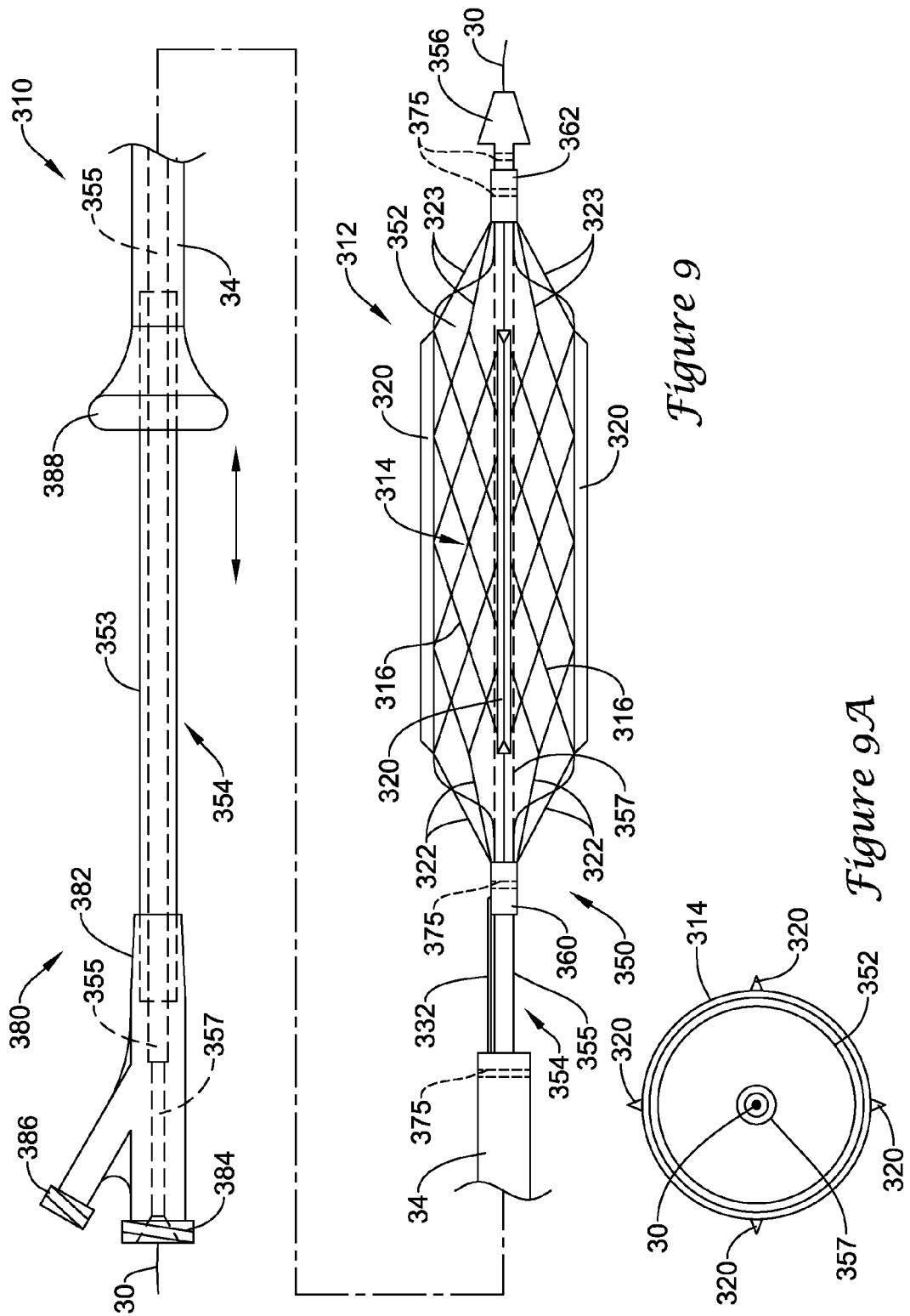
FIG. 9 is a side view of another exemplary system with cutting elements for incising a stenotic lesion.

FIG. 9 is a side view of another exemplary medical device assembly 310 for incising a stenosis in a blood vessel, or other lesion in an anatomical passage. The medical device assembly 310 may include an incising device 312 including one or more, or a plurality of cutting elements 320 for incising or scoring a stenosis within a blood vessel. Similar to the medical device assembly 10 of FIG. 1, the medical device assembly 310 may also include a tubular sheath 34 for delivering the incising device 312 to the stenotic lesion in the blood vessel and/or withdrawing the incising device 312 from the blood vessel.

The incising device 312 may be similar to the incising devise 12 in many respects. For example, the incising device 312 may include an expandable scaffold 314 carrying the one or more, or a plurality of cutting elements 320 thereon, and be configured to radially expand from a first, contracted configuration when radially constrained to a second, radially expanded configuration when unconstrained. In some instances, the expandable scaffold 314 may be a self-expanding scaffold 314 configured to automatically radially expand from the first, contracted configuration when radially constrained to the second, radially expanded configuration when unconstrained. Thus, the self-expanding scaffold 314 may be biased to the radially expanded configuration such that the self-expanding scaffold 314 tends to automatically return to the expanded configuration when all radially constraining forces are removed. In other instances, the expandable scaffold 314 may be expanded from the first, radially contracted configuration to the second radially expanded configuration through the application of an expansion force exerted by an expandable member, an expandable linkage, or other actuatable structure for expanding the scaffold 314.

The expandable scaffold 314 may have any desired construction permitting the expandable scaffold 314 to be radially compressed into the contracted configuration for positioning in the lumen 38 of the sheath 34, yet permitting the expandable scaffold 314 to radially expand to the expanded configuration when unconstrained by the sheath 34. For example, as shown in FIG. 9, the expandable scaffold 314 may be formed of a unitary tubular mesh framework of interconnected struts 316, similar to the structure of an expandable stent. At least some of the interconnected struts 316 may extend between adjacent cutting elements 320 within the tubular body portion of the expandable scaffold 314 to provide stability between adjacent cutting elements 320. For instance, at least a portion of the interconnected struts 316 may, at least in part, extend circumferentially around the circumference of the expandable scaffold 314 such that interconnected struts 316 extend between adjacent cutting elements 320 around the tubular body portion.

The tubular mesh framework 316 may define a cylindrical body portion of the expandable scaffold 314. The expandable scaffold 314 may also include one or more, or a plurality of proximally extending extension wires 322 extending from the proximal end of the tubular mesh framework 316 to a proximal tubular collar 360 positionable around a tubular shaft of a balloon catheter 350. The expandable scaffold 314 may additionally include one or more, or a plurality of distally extending extension wires 323 extending from the distal end of the tubular mesh framework 316 to a distal tubular collar 362 positionable around a tubular shaft of the balloon catheter 350.

The medical device assembly 310 may also include a balloon catheter 350 including an inflatable balloon 352 secured to the catheter shaft 354 of the balloon catheter 350 at a proximal balloon waist 358 and a distal balloon waist 359. In some instances, the catheter shaft 354 may include an inner tubular member 357 defining a guidewire lumen extending coaxially within an outer tubular member 355, defining an annular inflation lumen therebetween for inflating the inflatable balloon 352. A hypotube 353 may extend over a proximal portion of the outer tubular member 355 to provide column support to the proximal portion of the catheter shaft 354. In other embodiments, the catheter shaft 354 may be provided with another configuration, such as first and second parallel tubular members to define a guidewire lumen and an inflation lumen, respectively.

The proximal collar 360 may surround the catheter shaft 354 proximal of the inflatable main portion of the balloon 352, such as around the outer tubular member 355 of the catheter shaft 354 proximate to and/or proximal of the proximal balloon waist 358. Similarly, the distal collar 362 may surround the catheter shaft 354 distal of the inflatable main portion of the balloon 352, such as around the inner tubular member 357 of the catheter shaft 354 proximate to and/or distal of the distal balloon waist 359. The proximal collar 360 and/or the distal collar 362 may be configured to rotate and/or translate relative to the catheter shaft 354 in some instances.

The catheter 350 may also include a distal tip 356, such as an enlarged distal tip positioned distal of the distal collar 362, and thus distal of the balloon 352 and the expandable scaffold 314 surrounding the balloon 352. In some instances, the distal tip 356 may function as a distal stop to prevent the distal collar 362 from being removed from the catheter shaft 354. The expandable scaffold 314 may be permitted to have a limited amount of longitudinal movement relative to the catheter shaft 354, as well as rotational movement about the catheter shaft 354. Movement of the proximal and distal collars 360, 362 may facilitate expansion and contraction of the expandable scaffold 314 about the balloon 352. The distal tip 356 may have a lumen extending therethrough for the passage of a guidewire 30. In some instances such as shown in FIG. 3A, the distal tip 356, and thus the guidewire 30 extending through the central lumen of the distal tip 356, may be arranged coaxially with the expandable scaffold 314 and the balloon 352 of the balloon catheter 350, with the balloon 352 coaxially positioned within the expandable scaffold 314. In some instances, the distal tip 356 may also provide an atraumatic tip to the sheath 34 when the incising device 312 is retracted into the lumen 38 of the sheath 34. Thus, in some instances, the distal tip 356, or a portion thereof, may be sized to remain exterior and distal of the sheath 34 when the expandable scaffold 314 of the incising device 312 is positioned within the sheath 34 during delivery and/or retrieval.

In some instances, the incising device 312 may also include an elongate member 332 extending proximally from the proximal collar 360 along an exterior of the catheter shaft 354 to be manipulated by a physician during a medical procedure to facilitate expelling the expandable scaffold 314 from the sheath 34, drawing the expandable scaffold 314 into the sheath 34, or otherwise manipulating the expandable scaffold 314. The elongate member 332 and the catheter shaft 354 may extend through the lumen 38 of the sheath 34 to a proximal end of the medical device assembly 310.

In some instances, the proximal tapered portion provided by the extension wires 322 may facilitate positioning the sheath 34 back over the expandable scaffold 314 to radially contract the expandable scaffold 314 after use of the incising device 312. For instance, the one or more proximally extending extension wires 322 may help guide the sheath 34 over the expandable scaffold 314 when collapsing the expandable scaffold 314 in the sheath 34 subsequent to using the incising device 312.

The cutting elements 320 may vary in number, position, and arrangement about the expandable scaffold 314. For example, the incising device 312 may include one, two, three, four, five, six, or more cutting elements 320 that are disposed at any position along the expandable scaffold 314 and in a regular, irregular, or any other suitable pattern. For example, in some embodiments the incising device 312 may include a plurality of cutting elements 320 longitudinally arranged symmetrically around the circumference of the expandable scaffold 314.

As shown in FIG. 9A, the cutting elements 320 may be mounted to and project radially outward from the expandable scaffold 314. In other embodiments, the struts 316 of the expandable scaffold 314 may define the cutting elements 320 for scoring or cutting tissue. The cutting elements 320 may be secured to the struts 316 of the expandable scaffold 314 such as by welding, brazing, soldering, crimping, adhesively bonding, thermal bonding, or other desired means.

The balloon 352 of the balloon catheter 350 may be positioned in the interior of the expandable scaffold 314 to provide a radially outward force to urge the cutting elements 320 radially outward and press the cutting elements 320 against a stenosis or other tissue. For instance, the balloon 352 of the catheter 350 may be integrally incorporated with the incising device 312, and thus pre-inserted within the expandable scaffold 314 of the incising device 312 prior to using the incising device 312 in a medical procedure. In other instances, however, the incising device 312 may be provided without a balloon 352 pre-inserted within the expandable scaffold 314, thus allowing a physician to select any desired balloon 352 or other radially expandable member of a catheter 350 to be inserted within the expandable scaffold 314 intra-operatively, and/or allow for exchanging between a plurality of different sizes of balloons 352 intra-operatively.

The catheter shaft 354 and sheath 34 may extend proximally to a proximal handle assembly 380 at a proximal end of the medical device assembly 310 to be manipulated by a user. The handle assembly 380 may include a manifold 382 coupled to the proximal end of the catheter shaft 354. For example, the proximal end of the hypotube 354, the proximal end of the outer tubular member 355 and/or the proximal end of the inner tubular member 357 may be secured to the manifold 382, such as with an adhesive, or other bonding method. As shown in FIG. 9, the proximal end of the hypotube 353 and the proximal end of the outer tubular member 355 may extend into the manifold 382 with the proximal end of the outer tubular member 355 extending proximal of the proximal end of the hypotube 353. The proximal end of the inner tubular member 357 may extend proximally beyond the proximal end of the outer tubular member 355. The manifold 382 may include one or more ports, such as a guidewire port 384 in communication with the guidewire lumen of the inner tubular member 357 from which the guidewire 30 may extend from, and an inflation port 386 in fluid communication with the inflation lumen between the inner tubular member 357 and the outer tubular member 355 in which an inflation media may be delivered to the interior of the balloon 352 through the inflation lumen.

The handle assembly 380 may also include an actuation member 388, such as a push-pull knob or handle, coupled to the proximal end of the sheath 34 for manipulation of the sheath 34 to deploy and/or retrieve the incising device 312. In other instances, the handle assembly 380 may include an alternative structure configured for actuating the sheath 34. Some additional structures may include a dial, a thumb push/pull lever, or other structure to effect actuation of the sheath 34 relative to the catheter shaft 354. A user may manipulate the actuation member 388 to translate the sheath 34 in a proximal direction and/or a distal direction in order to withdraw the sheath 34 from the expandable scaffold 314 and/or advance the sheath 34 over the expandable scaffold 314, respectively. In some instances, the actuation member 388 may include a locking mechanism to prevent inadvertent relative movement between the sheath 34 and the catheter shaft 354 to prevent premature deployment of the expandable scaffold 314 from the sheath 34. In some instances, a distal end of the hypotube 353 may be located proximate the actuation member 388 when the sheath 34 has been pulled proximally to withdraw the sheath 34 from the expandable scaffold 314.

The medical device assembly 310, as well as the medical device assemblies 10, 110 and 210, may also include radiopaque marker bands 375 positioned on or incorporated in various components of the assembly 310 in order to permit visual observation of the assembly 310 in a body vessel under fluoroscopy or other visualization technique. For example, the sheath 34 may include a radiopaque marker band 375 proximate the distal end of the sheath 34. Furthermore, the catheter shaft 356 may include radiopaque marker bands 375 positioned proximal and distal of the balloon 352 and/or the proximal and distal collars 360, 362 may include radiopaque marker bands 375 or be formed of a radiopaque material to facilitate positioning the incising device 312 across a stenosis. Additionally, the distal tip 356 may include a radiopaque marker band 375 or be formed of a radiopaque material in order to visualize the position of the distal tip 356 in a vessel. Additional radiopaque markers may be incorporated into the expandable scaffold 314 or other components of the medical device assembly 310, as desired.

FIGS. 10-14 illustrate an exemplary method of treating a stenotic lesion with the medical device assembly 310 illustrated in FIG. 9. Although the exemplary method will be described in regards to using the medical device assembly 310, it is understood that such a method of treating a stenosis may be performed using any of the assemblies and incising device described herein, or a similarly configured incising device in accordance with this disclosure.

The medical device assembly 310 may be navigated through the lumen 92 of a blood vessel 90 to a treatment location proximate a stenosis 94 or other tissue to be treated which may be within any suitable peripheral or cardiac vessel lumen location. For instance, the incising device 312 may be loaded in the sheath 34 with the expandable scaffold 314 constrained in the contracted position within the lumen 38 of the sheath 34 prior to advancing the medical device assembly 10 through the blood vessel 90. The distal tip 356 may be located at the distal end of the sheath 34, providing an atraumatic tip for insertion of the medical device assembly 310 through the vasculature.

Figure 10:
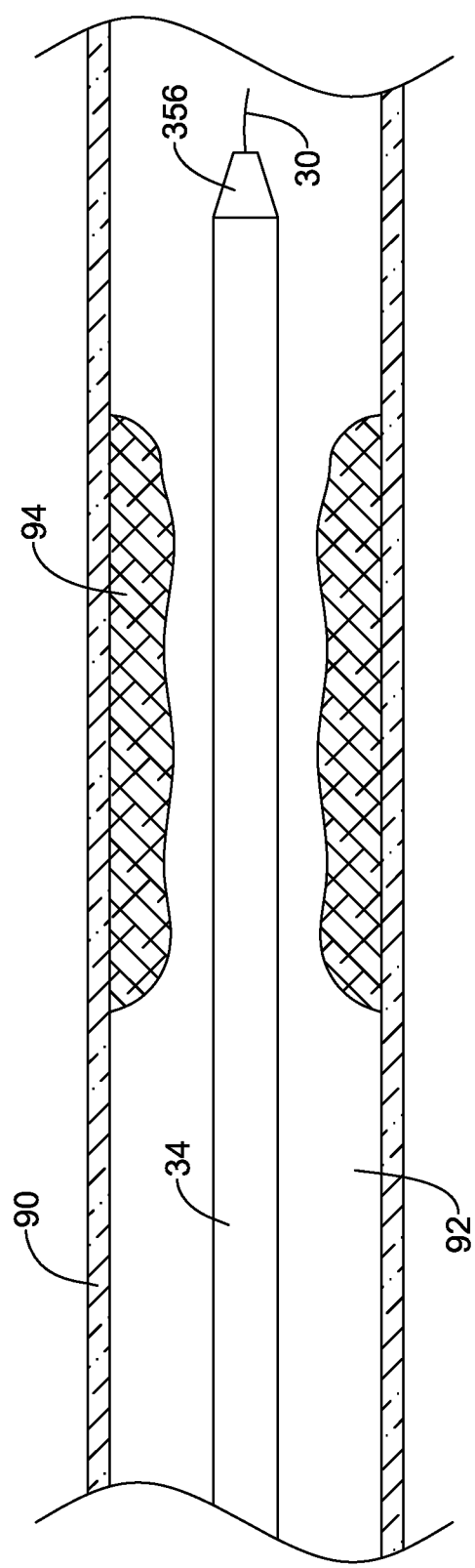
FIGS. 10-14 illustrate an exemplary method of treating a stenotic lesion with the incising system of FIG. 9.

The distal tip 356 may be inserted over a previously positioned guidewire 30, with the guidewire 30 extending through the interior of the expandable scaffold 314 and through the lumen 38 of the sheath 34. As shown in FIG. 10, sheath 34, with the expandable scaffold 314 of the incising device 312 positioned therein, may be advanced to the stenosis 94 in the blood vessel 90. The guidewire 30 may extend through a guidewire lumen of the catheter shaft 354 of the catheter 350, which extends within the lumen 38 of the sheath 34. The sheath 34 may be advanced across the stenosis 94 until the expandable scaffold 314 is properly positioned. Radiopaque marker bands 275 incorporated with the components of the medical device assembly 310 may be used to visually confirm the position of the expandable scaffold 314 across the stenosis 94 using fluoroscopy or other visualization technique.

Figure 11:
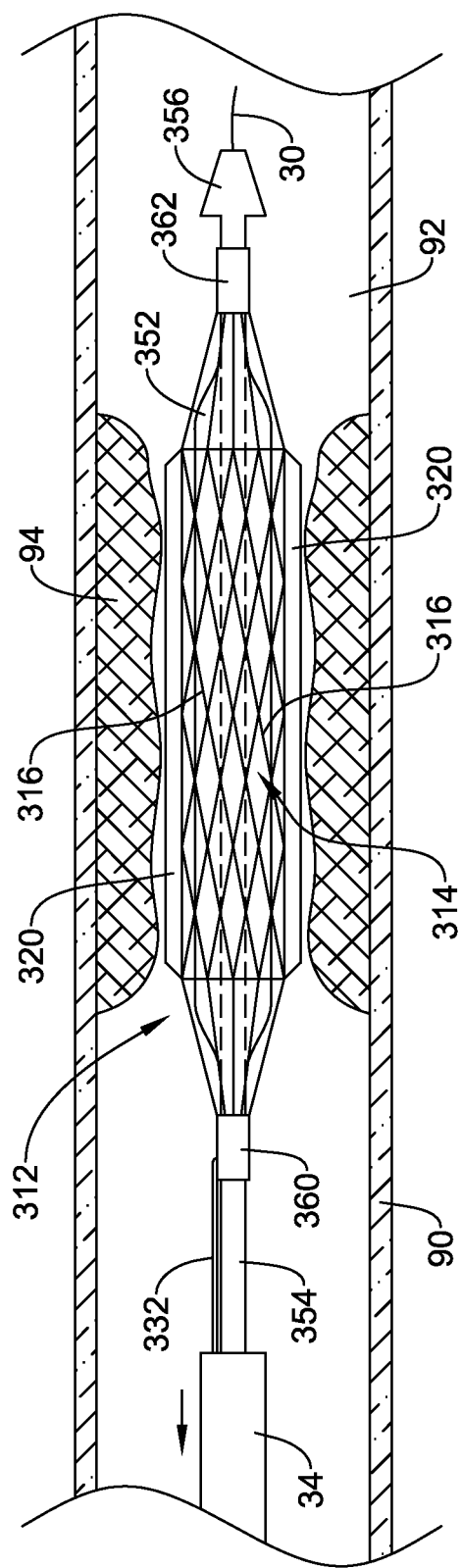

As shown in FIG. 11, once the radially constrained expandable scaffold 314 is positioned across the stenosis 94 within the sheath 34, the sheath 34 may be withdrawn proximally to deploy the expandable scaffold 314 distally from the distal opening 36 of the tubular sheath 34. For example, the physician may pull the actuation member 388, or otherwise actuate the actuation member 388, to withdraw the sheath 34 proximally to deploy the expandable scaffold 314 from the distal end of the sheath 34. Radiopaque marker bands 275 incorporated with the components of the medical device assembly 310 may be used to visually confirm the position of the distal end of the sheath 34 relative to the expandable scaffold 314 to ensure of proper deployment of the expandable scaffold 314 using fluoroscopy or other visualization technique.

The protective distal tip 40 of the sheath 34 may withstand scoring from the cutting elements 320 as the incising device 312 is advanced out of the lumen 38 through the distal opening 36. Once unconstrained by the sheath 34, the expandable scaffold 314, in instances in which the scaffold 314 is self-expandable, may automatically radially expand toward the expanded configuration. The expandable scaffold 314 may be sized such that in the expanded configuration, the cutting elements 320 may contact and/or press against the stenosis 94.

Figure 12:
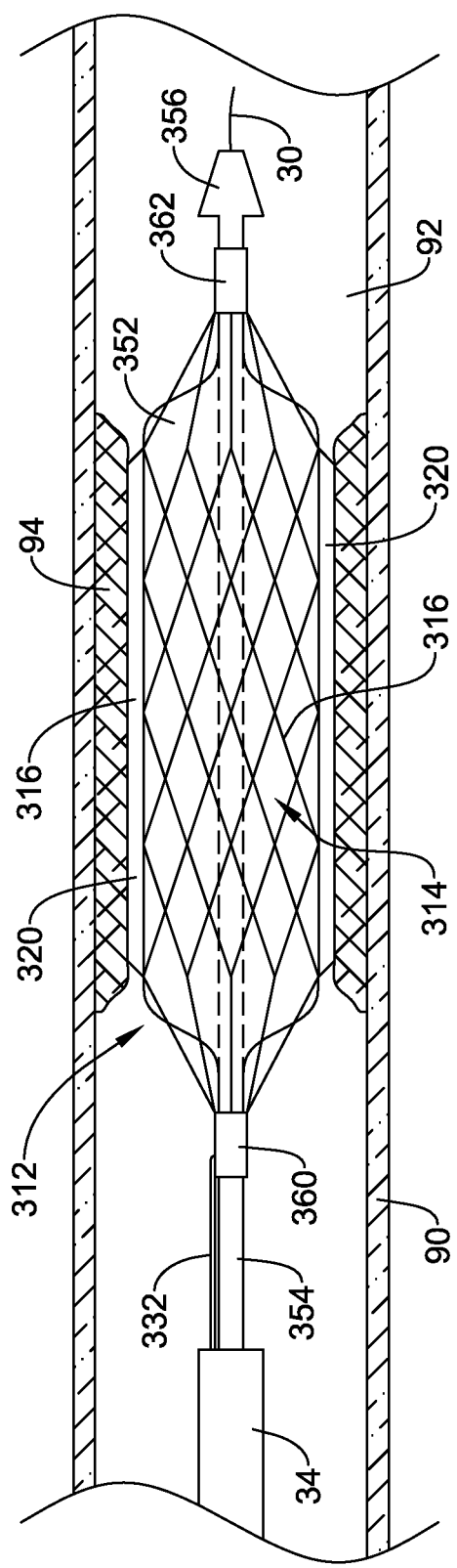

As shown in FIG. 12, the deflated balloon 352 of the catheter 350, positioned within the expandable scaffold 314 can be inflated to exert a radially outward force on the interior of the expandable scaffold 314 to further enlarge the expandable scaffold 314 and/or to urge the cutting elements 320 further radially outward to penetrate into or score the stenosis 94. Thus, the cutting elements 320 may cut or score the stenosis 94 to facilitate enlarging the lumen proximate the stenosis 94. Subsequently, the balloon 352 may be deflated within the interior of the expandable scaffold 314.

Figure 13:
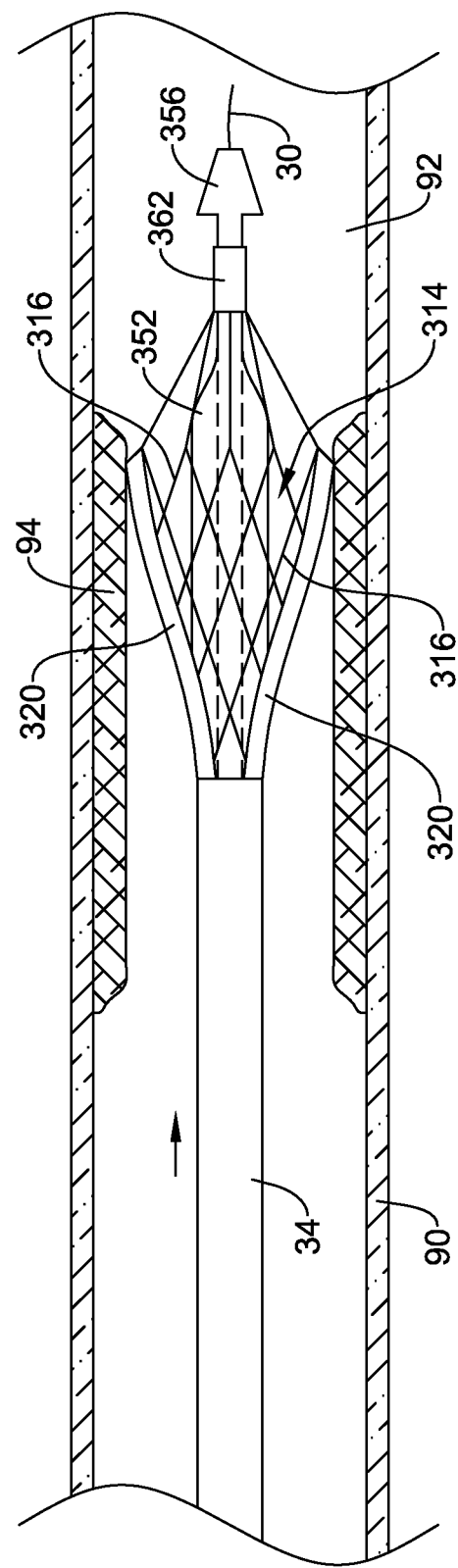

As shown in FIG. 13, once the desired treatment of the blood vessel 90 with the incising device 312 has been achieved, the incising device 312 may be recaptured and retrieved with the sheath 34, and then withdrawn from the blood vessel 90. For example, as shown in FIG. 13, the sheath 34, or another sheath, may be advanced distally to the expandable scaffold 314. For example, the actuation member 388 may be actuated distally relative to the elongate shaft 354, or otherwise actuated, to advance the sheath 34 distally over the expandable scaffold 314 and thus collapse the expandable scaffold 314 into the lumen 38 of the sheath 34. The protective distal tip 40 of the sheath 34 may withstand scoring from the cutting elements 320 as the incising device 312 is retracted into the lumen 38 through the distal opening 36.

Figure 14:
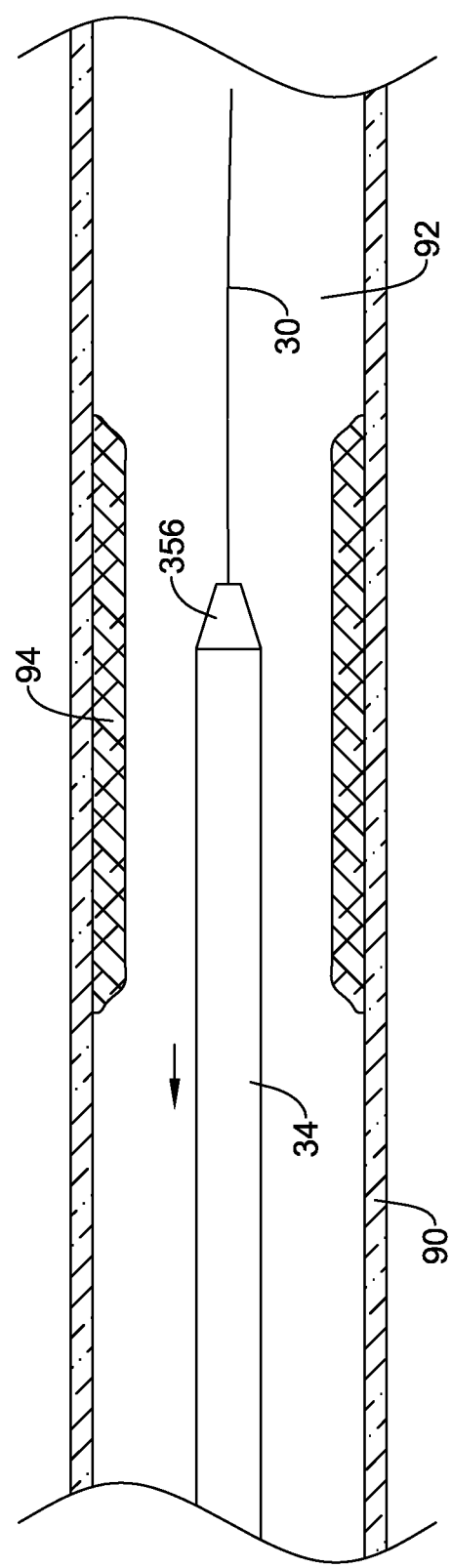

As shown in FIG. 14, the sheath 34 may be advanced distally until the expandable scaffold 314 is within the sheath 34 and the distal tip 356 is located at the distal end of the sheath 34. Radiopaque marker bands 275 may be used to visually confirm the position of the expandable scaffold 314 within the lumen 38 of the sheath 34 and/or the distal tip 356 at the distal end of the sheath 34 using fluoroscopy or other visualization technique. The sheath 34 and incising device 312 may then be withdrawn from the blood vessel 90, leaving the guidewire 30 in place for navigating additional medical devices across the stenosis 94 in the blood vessel 90, if desired.

The above described features of expandable scaffolds including cutting elements may permit the cutting elements to be delivered to a stenotic lesion in a blood vessel without being directed mounted to an angioplasty balloon. The scaffolding, with the cutting members secured thereto, may be more flexible for navigating tortuous anatomy, while securely delivering the cutting elements to the treatment site.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A medical device assembly for incising a stenosis in a blood vessel, the medical device assembly comprising:
   a self-expanding scaffold configured to be expandable from a first contracted configuration to a second expanded configuration, the self-expanding scaffold being biased toward the second expanded configuration;
   a cutting element secured to the self-expanding scaffold and extending radially outward therefrom;
   a sheath having a lumen therein, the self-expanding scaffold positionable in the lumen of the sheath in the first contracted configuration;
   an elongate member extending proximally from the self-expanding scaffold through the lumen of the sheath;
   an inflatable balloon mounted on a catheter slidably disposed within the lumen of the sheath;
   and a guidewire disposed within the lumen of the sheath;
   wherein the self-expanding scaffold is constrained by the sheath to maintain the self-expanding scaffold in the first contracted configuration in the lumen of the sheath, and deployed out of the lumen of the sheath to permit the self-expanding scaffold to expand to the second expanded configuration
   and wherein the catheter includes a distal tip configured to contact the distal tip of the self-expanding scaffold when the inflatable balloon is properly positioned within the interior of the self-expanding scaffold.

2. A medical device assembly for incising a stenosis in a blood vessel the medical device assembly comprising:
   a self-expanding scaffold configured to be expandable from a first contracted configuration to a second expanded configuration, the self-expanding scaffold being biased toward the second expanded configuration;
   a cutting element secured to the self-expanding scaffold and extending radially outward therefrom;
   a sheath having a lumen therein, the self-expanding scaffold positionable in the lumen of the sheath in the first contracted configuration;
   an elongate member extending proximally from the self-expanding scaffold through the lumen of the sheath;
   an inflatable balloon mounted on a catheter slidably disposed within the lumen of the sheath;
   and a guidewire disposed within the lumen of the sheath wherein the catheter is configured to be advanced through the lumen of the sheath over the guidewire;
   wherein the self-expanding scaffold is constrained by the sheath to maintain the self-expanding scaffold in the first contracted configuration in the lumen of the sheath, and deployed out of the lumen of the sheath to permit the self-expanding scaffold to expand to the second expanded configuration; and
   wherein the catheter includes a distal tip configured to contact the distal tip of the self-expanding scaffold when the inflatable balloon is properly positioned within the interior of the self-expanding scaffold.

3. A medical device, assembly for incising a stenosis in a blood vessel, the medical device assembly comprising:
   a self-expanding scaffold configured to be expandable from a first contracted configuration to a second expanded configuration, the self-expanding scaffold being biased toward the second expanded configuration;
   a cutting element secured to the self-expanding scaffold and extending radially outward therefrom;
   a sheath having a lumen therein, the self-expanding scaffold positionable in the lumen of the sheath in the first contracted configuration;

an elongate member extending proximally from the self-expanding scaffold through the lumen of the sheath;

an inflatable balloon mounted on a catheter slidably disposed within the lumen of the sheath; wherein the elongate member extends along an exterior of the catheter; and a guidewire disposed within the lumen of the sheath, wherein the catheter is configured to be advanced through the lumen of the sheath over the guidewire;

wherein the self-expanding scaffold is constrained by the sheath to maintain the self-expanding scaffold in the first contracted configuration in the lumen of the sheath, and deployed out of the lumen of the sheath to permit the self-expanding scaffold to expand to the second expanded configuration; and wherein the catheter includes a distal tip configured to contact the distal tip of the self-expanding scaffold when the inflatable balloon is properly positioned within the interior of the self-expanding scaffold.

4. A medical device assembly for incising a stenosis in a blood vessel, the medical device assembly comprising:

an incising device including an expandable scaffold having a plurality of cutting elements projecting radially outward therefrom, and an elongate member extending proximally from the expandable scaffold to be manipulated by a user;

a tubular sheath having a lumen there through, the expandable scaffold positionable in the lumen of the tubular sheath in a contracted configuration with the plurality of cutting elements engaged with an interior of the tubular sheath;

a guidewire disposed within the lumen of the tubular sheath;

and a catheter having an inflatable balloon mounted thereon, the inflatable balloon of the catheter configured to be advanced distally into an interior of the expandable, scaffold through a proximal opening of the expandable scaffold;

wherein inflation of the inflatable balloon urges the cutting elements radially outward to incise a stenosis;

wherein the expandable scaffold is advanceable over the guidewire, the guidewire being positioned along an exterior surface of the elongate member and wherein the catheter includes a distal tip configured to contact a proximal end of the distal tip of the incising element when the inflatable balloon is properly positioned within the interior of the expandable scaffold.

5. A method of incising a stenosis in a brood vessel, the method comprising:

advancing a self-expanding scaffold of an incising device in a contracted configuration within a lumen of a tubular sheath to a stenosis in a blood vessel, the self-expanding scaffold including a plurality of cutting elements projecting radially outward therefrom and engaged with an interior of the tubular sheath;

withdrawing the tubular sheath from the self-expanding scaffold to permit the self-expanding scaffold to automatically expand radially outward to an expanded configuration to urge the cutting elements against the stenosis; advancing a deflated balloon of a balloon catheter through the tubular sheath and into an interior of the self-expanding scaffold through a proximal opening of the self-expanding scaffold with the self-expanding scaffold in the expanded configuration;

inflating the balloon to press against the interior of the self-expanding scaffold and press the cutting elements into the stenosis wherein the incising device includes a distal tip including a guidewire lumen for receiving a guidewire therethrough, the distal tip being arranged coaxially with the self-expanding scaffold;

and wherein the deflated balloon is advanced into the interior of the self-expanding scaffold until a distal tip of the catheter contacts a proximal end of the distal tip of the incising element when the deflated balloon is properly positioned within the interior of the self-expanding scaffold.

* * * * *